(12) United States Patent
Leyman et al.

(10) Patent No.: US 8,357,835 B2
(45) Date of Patent: Jan. 22, 2013

(54) USE OF TREHALOSE-6-PHOSPHATE SYNTHASE TO MODULATE PLANT GROWTH

(75) Inventors: Barbara Leyman, Ghent (BE); Matthew Ramon, Kortrijk (BE); Filip Rolland, Winksele (BE); Johan Thevelein, Blanden (BE); Patrick van Dijck, Zichem (BE); Lies Vandesteene, Kessel-Lo (BE)

(73) Assignees: VIB VZW, Ghent (BE); Katholieke Universiteit Leuven, K.U.Leuven R&D, Leuven (BE)

( * ) Notice: Subject to any disclaimer, the term of this patent is extended or adjusted under 35 U.S.C. 154(b) by 927 days.

(21) Appl. No.: 12/087,710

(22) PCT Filed: Jan. 29, 2007

(86) PCT No.: PCT/EP2007/000736
§ 371 (c)(1),
(2), (4) Date: Dec. 5, 2008

(87) PCT Pub. No.: WO2007/085483
PCT Pub. Date: Aug. 2, 2007

(65) Prior Publication Data
US 2010/0024066 A1    Jan. 28, 2010

(30) Foreign Application Priority Data

Jan. 27, 2006 (EP) .................................. 06100950
Apr. 19, 2006 (EP) .................................. 06112770

(51) Int. Cl.
*C12N 15/82* (2006.01)
(52) U.S. Cl. ........................................ 800/290; 800/284
(58) Field of Classification Search .................. None
See application file for complete search history.

(56) References Cited

U.S. PATENT DOCUMENTS

| | | | |
|---|---|---|---|
| 6,833,490 B1 * | 12/2004 | Goddijn et al. | 800/284 |
| 6,872,870 B1 | 3/2005 | Iturriaga de la Fuente et al. | |
| 2005/0283852 A1 | 12/2005 | De La Fuente et al. | |

FOREIGN PATENT DOCUMENTS

| | | |
|---|---|---|
| EP | 0 901 527 | 3/1999 |
| WO | WO 97/42326 | 11/1997 |
| WO | WO 97/42326 A | 11/1997 |
| WO | WO 00/22141 | 4/2000 |
| WO | WO 00/22141 A | 4/2000 |
| WO | WO 2007/085483 | 8/2007 |
| WO | WO 2007/085483 A1 | 8/2007 |

OTHER PUBLICATIONS

Schluepmann et al. 2002, PNAS 100(11): 6849.*
Eastman et al. 2003, J. Exp. Bot. 54: (382) 533-537.*
Eastmond et al; Is trehalose-6-phosphate a regulator of sugar metabolism in plants?; Journal of Experimental Botany, Vo. 54, No. 382; pp. 533-537, Jan. 2003.
Jang et al; Expression of a Bifunctional Fusion of the *Escherichia coli* Genes for Trehalose-6-Phosphate Synthase and Trehalose-6-Phosphate Phosphatase in Transgenic Rice Plants Increases Trehalose Accumulation and Abiotic Stress Tolerance without Stunting Growth; Plant Physiology, Feb. 2003; vol. 131, pp. 516-524.
Kolbe et al; Trehalose 6-phophate regulates starch synthesis via post-translational redox activation of ADP-glucose pyrophosphorylase; PNAS; Aug. 2, 2005, vol. 102, No. 31, pp. 11118-11123.
Leyman et al; An unexpected plethora of trehalose biosynthesis genes in *Arabidopsis thaliana*; Trends in Plant Science, vol. 6, No. 11, Nov. 2001, pp. 510-513.
Vogel, et al.; Trehalose metabolism in *Arabidoppsis*: Occurrence of trehalose and molecular cloning and characterization of trehalose-6-phosphate synthase homologues; Journal of Experimental Botany, vol. 52, No. 362, pp. 1817-1826, Sep. 2001.
Jang et al., Expression of a bifunctional fusion of the *Escherichia coli* genes for trehalose-6-phosphate synthase and trehalose-6-phosphate phosphatase in transgenic rice plants increases trehalose accumulation and abiotic stress tolerance without stunting growth, Plant Physiology, Feb. 2003, pp. 516-524, vol. 131, No. 2.
Eastmond et al., Is trehalose-6-phosphate a regulator of sugar metabolism in plants? Journal of Experimental Botany, Jan. 2003, pp. 533-537, vol. 54, No. 382.
Vogel et al., Trehalose metabolism in *Arabidopsis*: Occurrence of trehalose and molecular cloning and characterization of trehalose-6-phosphate synthase homologues, Journal of Experimental Botany, Sep. 2001, pp. 1817-1826, vol. 362, No. 52, Oxford University Press, GB.
Leyman et al., An unexpected plethora of trehalose biosynthesis genes in *Arabidopsis thaliana*, Trends in Plant Science, Nov. 2001, pp. 510-513, vol. 6, No. 11, Elsevier Science, Oxford, GB.
Kolbe et al., Trehalose 6-phosphate regulates starch synthesis via posttranslational redox activation of ADP-glucose pyrophosphorylase, Proceedings of the National Academy of Sciences of the United States of America, Aug. 2005, pp. 11118-11123, vol. 102, No. 31.
PCT International Search Report, PCT/EP2007/000736, dated May 9, 2007.
Harhill, et al.; Phosphorylation and 143-3 binding of *Arabidopsis* trehalosephosphate synthase 5 in response to 2-deoxyglucose; The Plant Journal (2006) 47, pp. 211-223.
Ramon, et al.; Extensive expression regulation and lack of heterologous enzymatic activity of the Class II trehalose metabolism proteins from *Arabidopsis thaliana*; Plant, Cell and Environment (2009) 32, pp. 1015-1032.

* cited by examiner

*Primary Examiner* — Anne Kubelik
*Assistant Examiner* — Lee A Visone
(74) *Attorney, Agent, or Firm* — TraskBritt

(57) ABSTRACT

The present invention relates to the use of trehalose-6-phosphate synthase to modulate plant growth. More specifically, it relates to the use of a class II trehalose-6-phosphate synthase, comprising both a synthase and a phosphatase-like part to modulate plant growth. Preferably, the activity of trehalose-6-phosphate synthase is down-regulated to obtain an increased plant biomass yield.

6 Claims, 12 Drawing Sheets

Rootlength of *AtTPS8* KO under different conditions
GT2-GT4-GT6 are different KO lines of *AtTPS8*
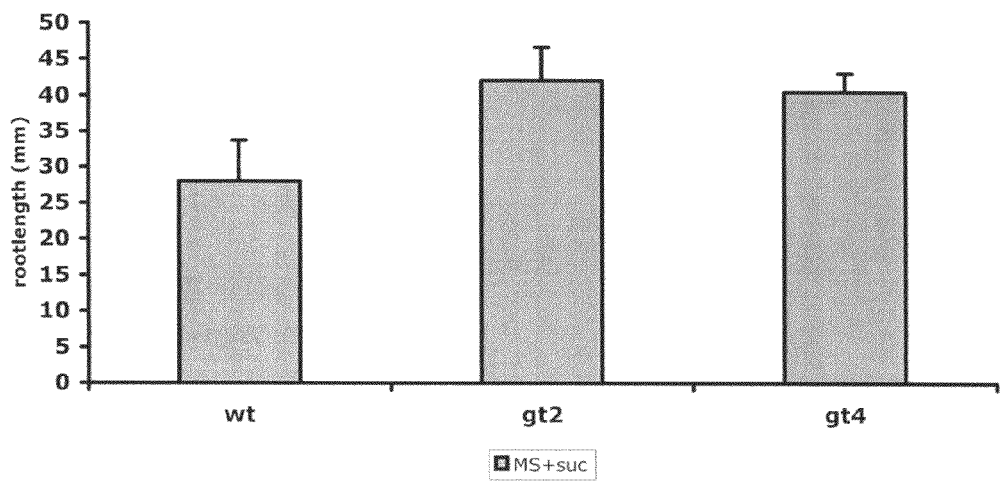
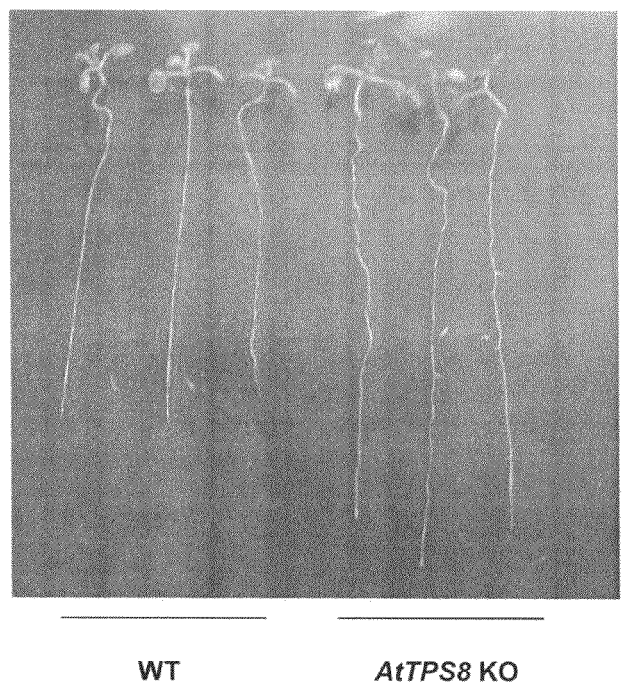
FIG. 1, page 1 of 4

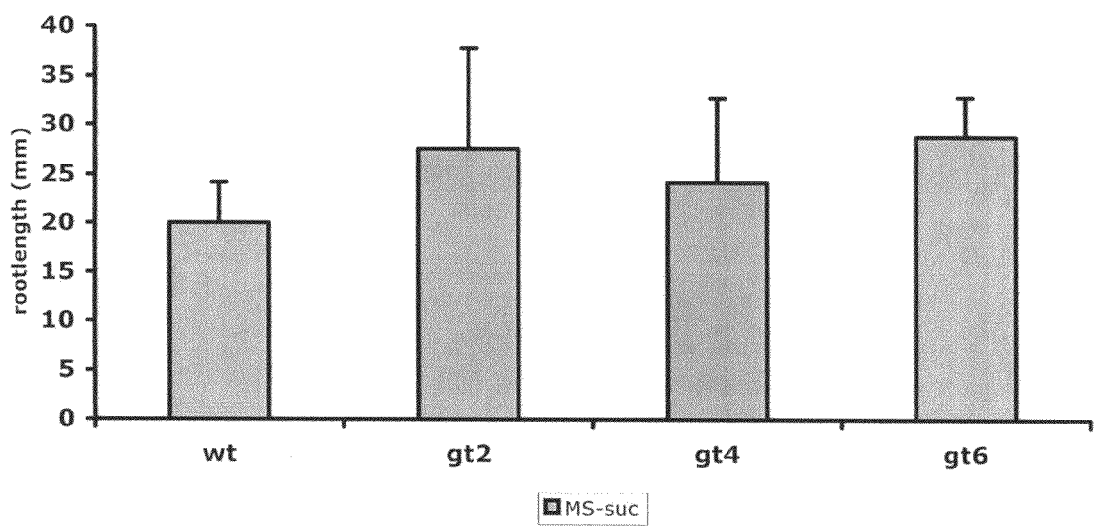
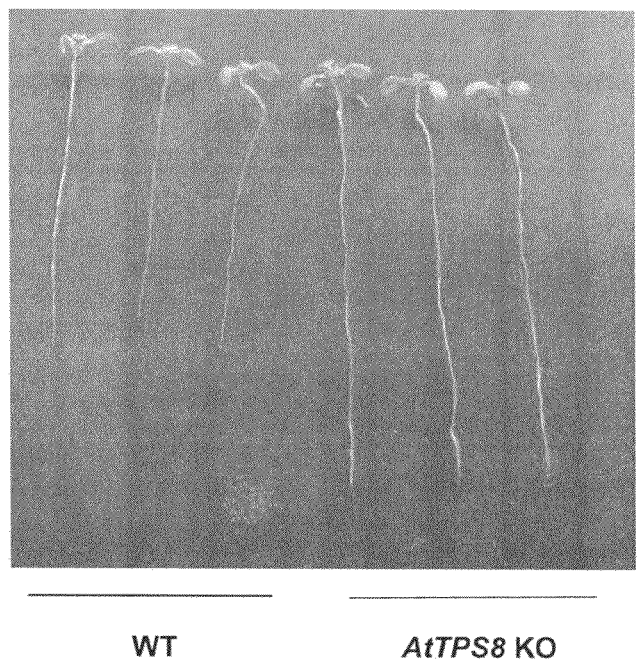
FIG. 1, page 2 of 4

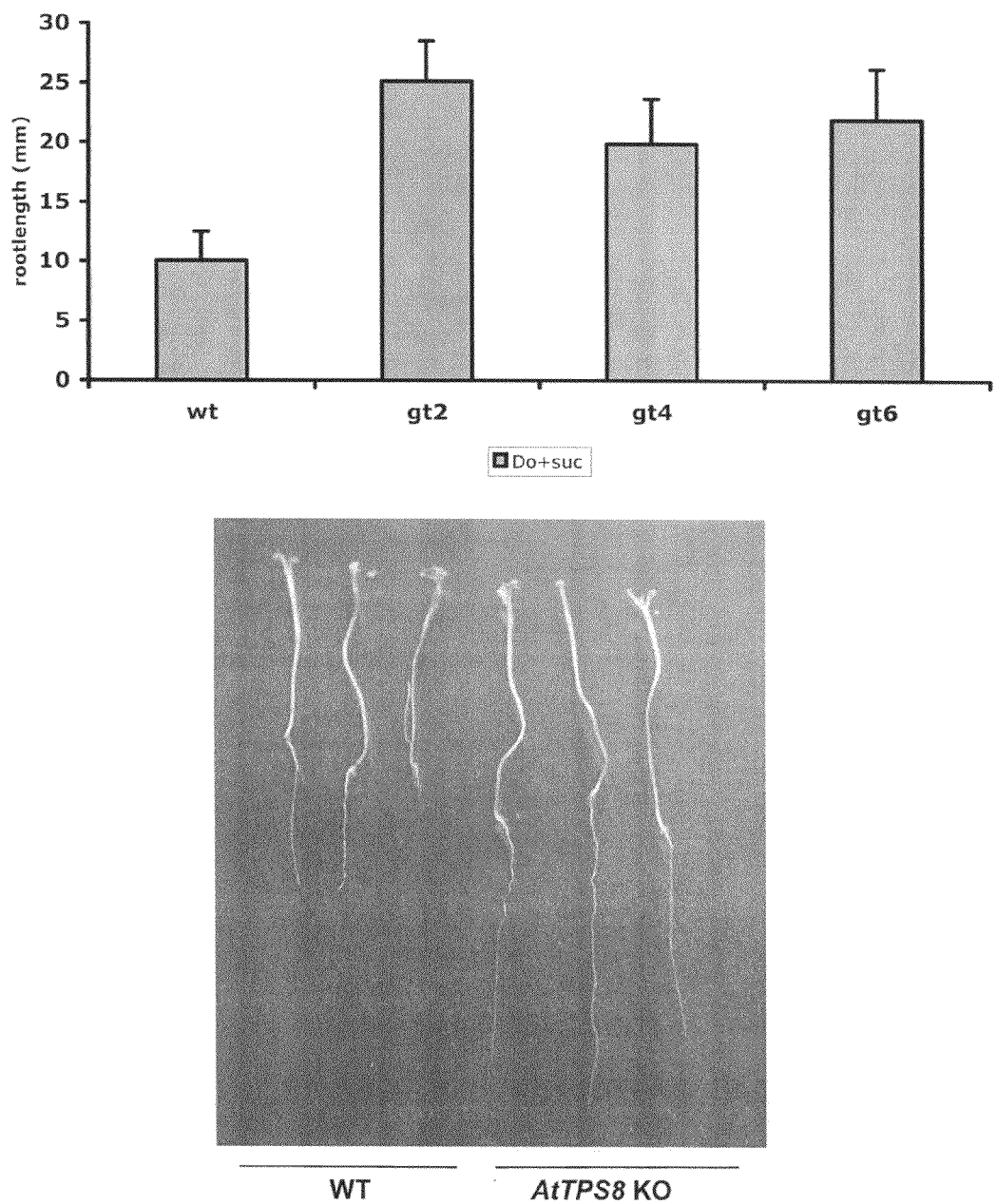
FIG. 1, page 3 of 4

*AtTPS8* KO lines -suc medium in the dark
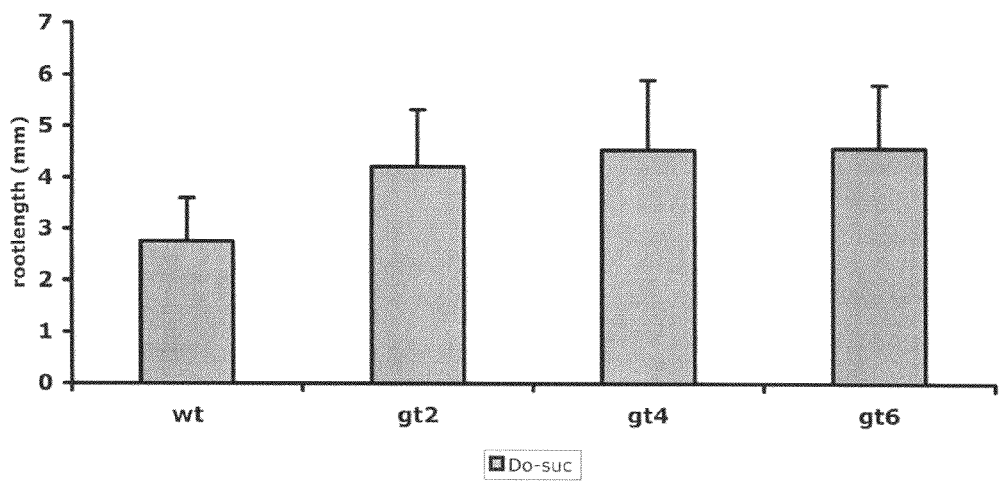
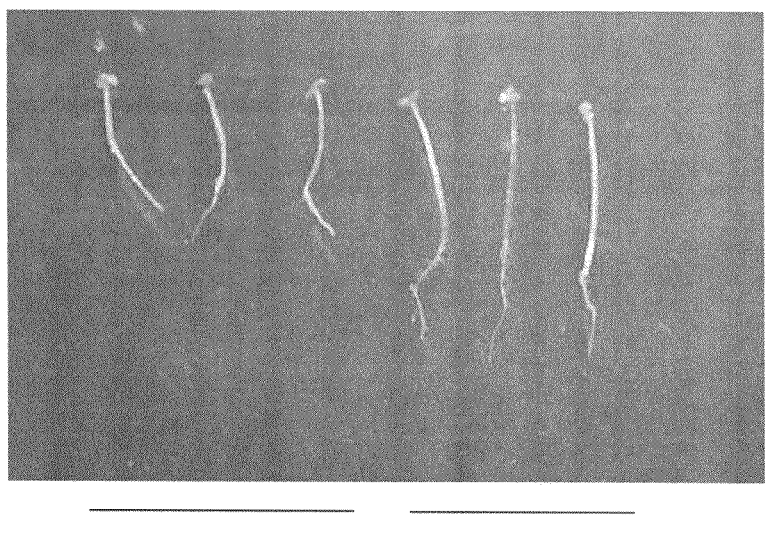
WT          *AtTPS8 KO*
FIG. 1, page 4 of 4

Expression levels of *AtCYCD3* and *ApL3*
in the *AtTPS8* KO background
ApL3 expression
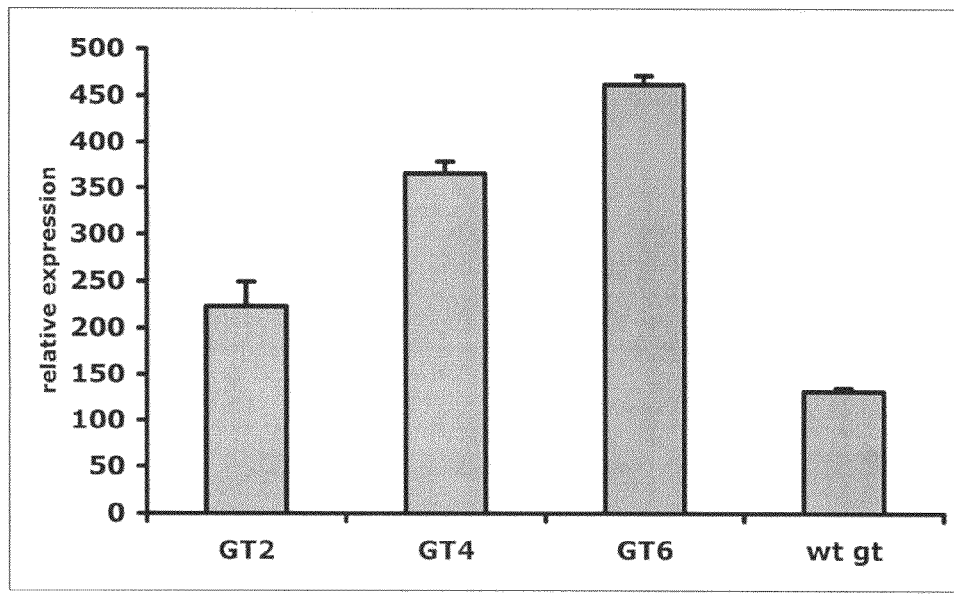
AtCYCD3 expression
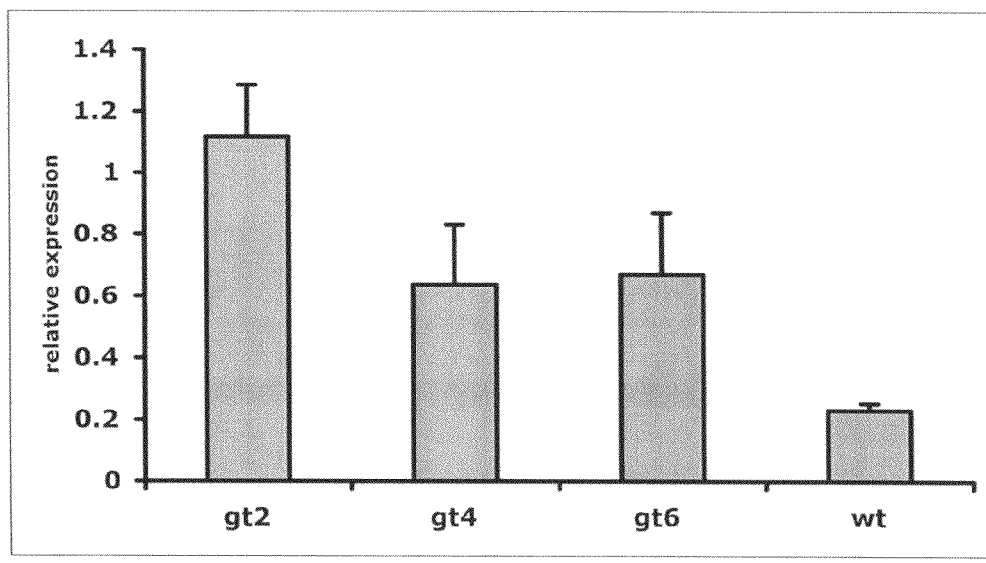
FIG. 2

**Phenotypic characterization of the adult *AtTPS8* KO compared to WT plants**
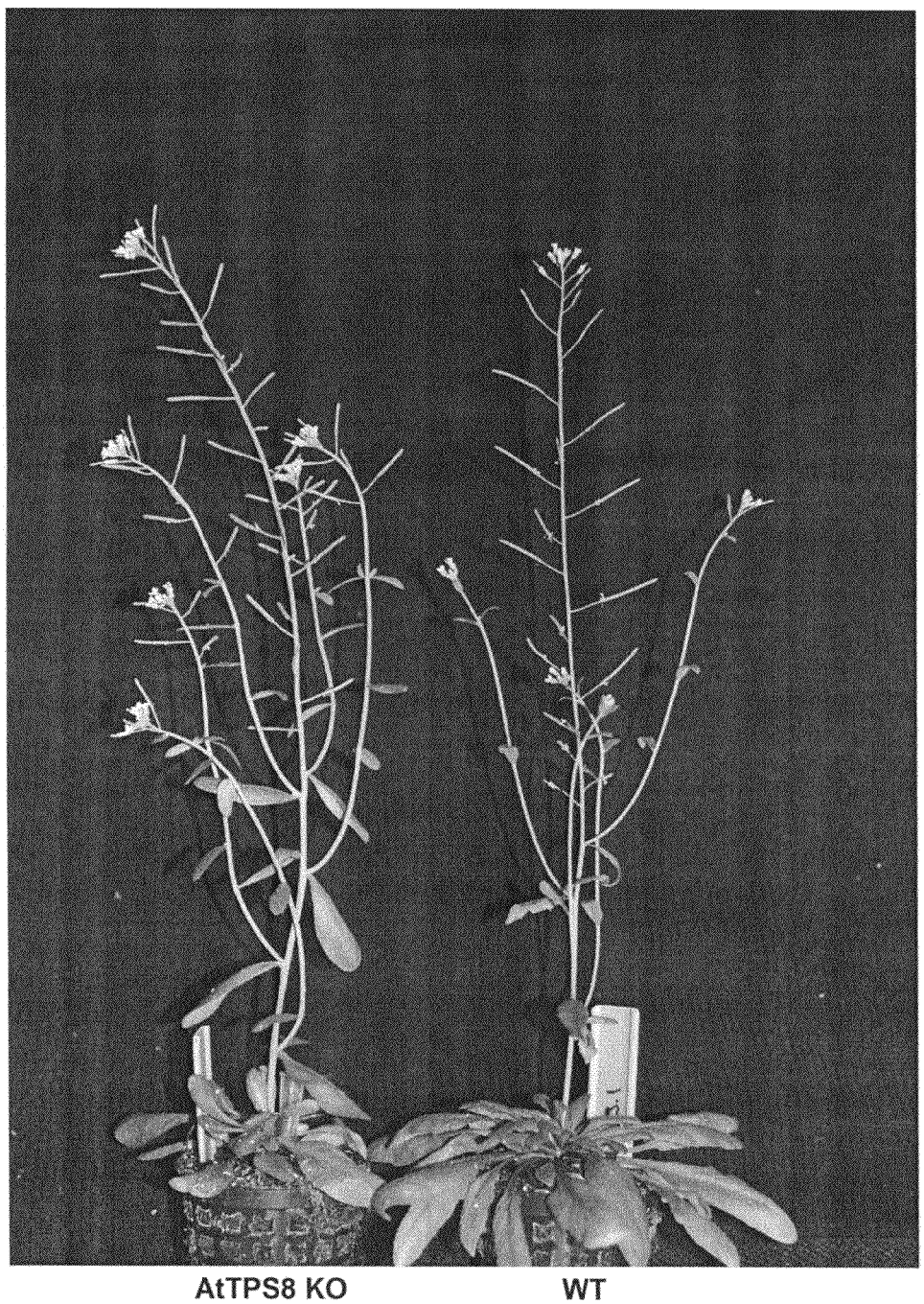
AtTPS8 KO          WT
FIG. 3, page 1 of 3

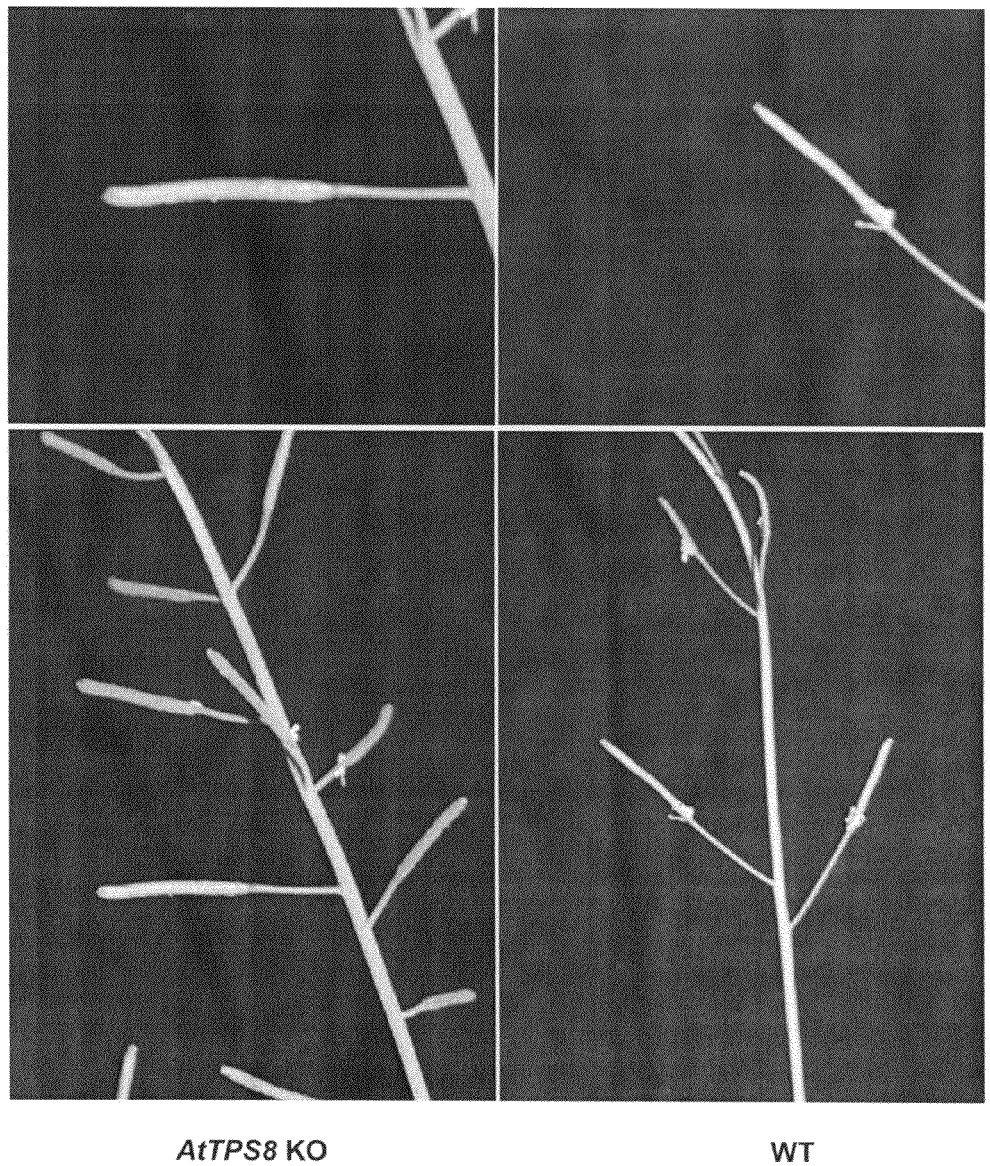
FIG. 3, page 2 of 3

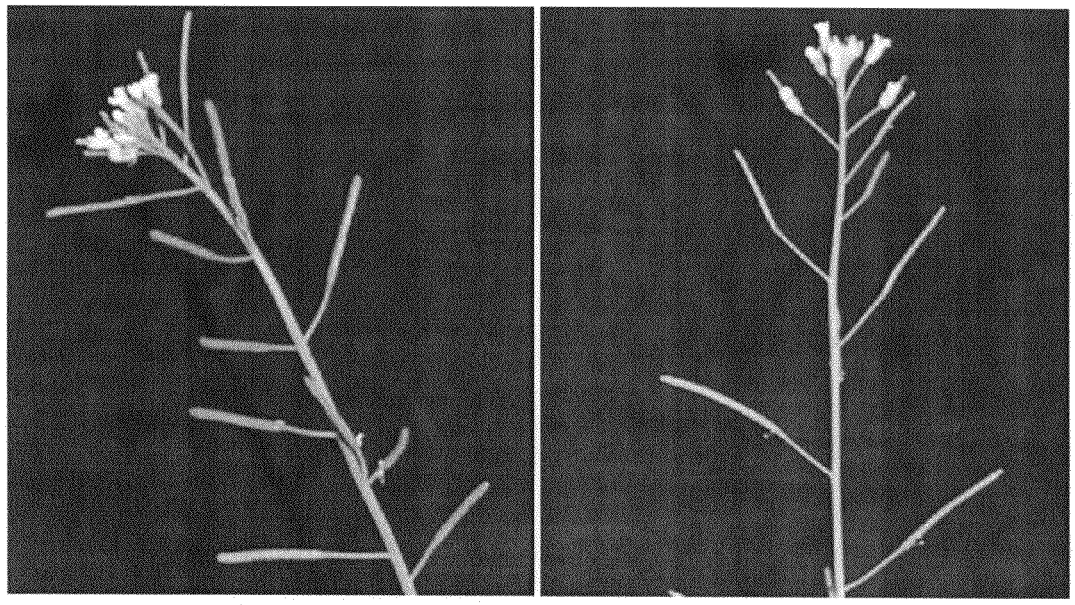
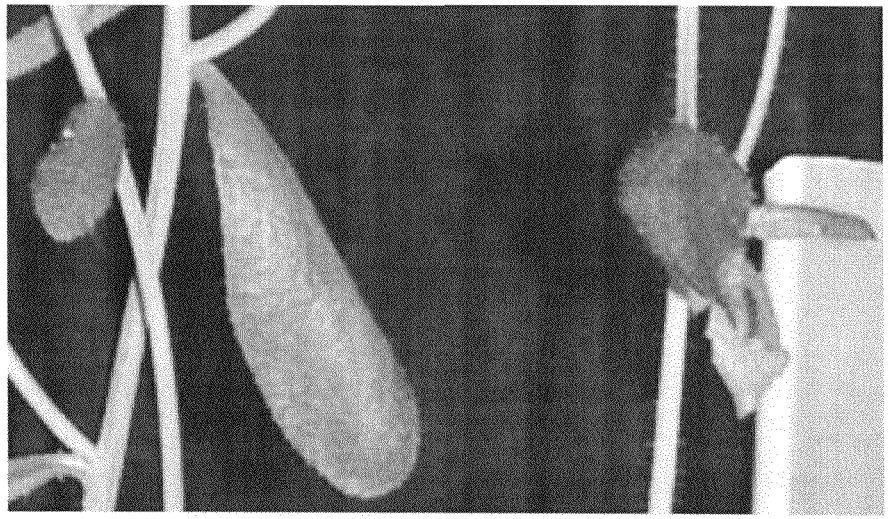
Cauline leaves
FIG. 3, page 3 of 3

1 X MS, 1% sucrose

1 X MS, 1% sucrose

SEQUENCE LISTING

<160> NUMBER OF SEQ ID NOS: 30

<210> SEQ ID NO 1
<211> LENGTH: 865
<212> TYPE: PRT
<213> ORGANISM: Arabidopsis thaliana

<400> SEQUENCE: 1

```
Met Ile Ser Asp Tyr Leu Arg His Cys Ile Tyr Phe Thr Cys Cys Arg
1               5                   10                  15

Asp Met Val Ser Arg Ser Tyr Ser Asn Leu Leu Asp Leu Ala Ser Gly
            20                  25                  30

Asn Phe His Ser Phe Ser Arg Glu Lys Lys Arg Phe Pro Arg Val Ala
        35                  40                  45

Thr Val Thr Gly Val Leu Ser Glu Leu Asp Asp Asn Asn Ser Asn
    50                  55                  60

Ser Val Cys Ser Asp Ala Pro Ser Ser Val Thr Gln Asp Arg Ile Ile
65                  70                  75                  80

Ile Val Gly Asn Gln Leu Pro Ile Lys Ser His Arg Asn Ser Ala Gly
                85                  90                  95

Lys Leu Ser Phe Ser Trp Asp Asn Asp Ser Leu Leu Leu Gln Leu Lys
            100                 105                 110
```

-continued

Asp Gly Met Arg Glu Asp Met Glu Val Val Tyr Ile Gly Cys Leu Lys
            115                 120                 125

Glu Gln Ile Asp Thr Val Gln Asp Val Ser Gln Arg Leu Leu
        130                 135                 140

Glu Asn Phe Lys Cys Val Pro Ala Tyr Ile Pro Pro Glu Leu Phe Thr
145                 150                 155                 160

Lys Tyr Tyr His Gly Phe Cys Lys Gln His Leu Trp Pro Leu Phe His
                165                 170                 175

Tyr Met Leu Pro Leu Thr Pro Asp Leu Gly Gly Arg Phe Asp Arg Ser
            180                 185                 190

Leu Trp Gln Ala Tyr Leu Ser Val Asn Lys Ile Phe Ala Asp Lys Val
        195                 200                 205

Met Glu Val Ile Ser Pro Asp Asp Phe Val Trp Val His Asp Tyr
    210                 215                 220

His Leu Met Val Leu Pro Thr Phe Leu Arg Lys Arg Phe Asn Arg Val
225                 230                 235                 240

Lys Leu Gly Phe Phe Leu His Ser Pro Phe Pro Ser Ser Glu Ile Tyr
                245                 250                 255

Arg Thr Leu Pro Val Arg Asn Glu Leu Leu Arg Ala Leu Leu Asn Ala
            260                 265                 270

Asp Leu Ile Gly Phe His Thr Phe Asp Tyr Ala Arg His Phe Leu Ser
        275                 280                 285

Cys Cys Ser Arg Met Leu Gly Leu Ser Tyr Gln Ser Lys Arg Gly Thr
    290                 295                 300

Ile Gly Leu Glu Tyr Tyr Gly Arg Thr Leu Gln Ser Ile Leu Asn Leu
305                 310                 315                 320

Pro Glu Thr Gln Thr Lys Val Ala Glu Leu Arg Asp Gln Phe Leu Asp
                325                 330                 335

Gln Lys Val Leu Leu Gly Val Asp Asp Met Asp Ile Phe Lys Gly Ile
            340                 345                 350

Ser Leu Lys Leu Leu Ala Met Glu Gln Leu Leu Thr Gln His Pro Glu
        355                 360                 365

Lys Arg Gly Arg Val Val Leu Val Gln Ile Ala Asn Pro Ala Arg Gly
    370                 375                 380

Arg Gly Lys Asp Val Gln Glu Val Gln Ser Glu Thr Glu Ala Thr Val
385                 390                 395                 400

Lys Arg Ile Asn Glu Met Phe Gly Arg Pro Gly Tyr Gln Pro Val Val
                405                 410                 415

Leu Ile Asp Thr Pro Leu Gln Phe Phe Glu Arg Ile Ala Tyr Tyr Val
            420                 425                 430

Ile Ala Glu Cys Cys Leu Val Thr Ala Val Arg Asp Gly Met Asn Leu
        435                 440                 445

Ile Pro Tyr Glu Tyr Ile Ile Cys Arg Gln Gly Asn Pro Lys Leu Asn
    450                 455                 460

Glu Thr Ile Gly Leu Asp Pro Ser Ala Ala Lys Lys Ser Met Leu Val
465                 470                 475                 480

Val Ser Glu Phe Ile Gly Cys Ser Pro Ser Leu Ser Gly Ala Ile Arg
                485                 490                 495

Val Asn Pro Trp Asn Ile Asp Ala Val Thr Glu Ala Met Asp Tyr Ala
            500                 505                 510

Leu Ile Val Ser Glu Ala Glu Lys Gln Met Arg His Glu Lys His His
        515                 520                 525

Lys Tyr Val Ser Thr His Asp Val Ala Tyr Trp Ala Arg Ser Phe Ile

```
                    530             535             540
Gln Asp Leu Glu Arg Ala Cys Gly Asp His Val Arg Lys Arg Cys Trp
545                 550                 555                 560

Gly Ile Gly Phe Gly Leu Gly Phe Arg Val Val Ala Leu Asp Pro Ser
                565                 570                 575

Phe Lys Lys Leu Ser Ile Glu His Ile Val Ser Ala Tyr Lys Arg Thr
                580                 585                 590

Lys Asn Arg Ala Ile Leu Leu Asp Tyr Asp Gly Thr Met Val Gln Pro
                595                 600                 605

Gly Ser Ile Arg Thr Thr Pro Thr Arg Glu Thr Ile Glu Ile Leu Asn
                610                 615                 620

Asn Leu Ser Ser Asp Pro Lys Asn Ile Val Tyr Leu Val Ser Gly Lys
625                 630                 635                 640

Asp Arg Arg Thr Leu Thr Glu Trp Phe Ser Cys Asp Asp Leu Gly
                645                 650                 655

Leu Gly Ala Glu His Gly Tyr Phe Ile Arg Pro Asn Asp Gly Thr Asp
                660                 665                 670

Trp Glu Thr Ser Ser Leu Val Ser Gly Phe Glu Trp Lys Gln Ile Ala
                675                 680                 685

Glu Pro Val Met Arg Leu Tyr Thr Glu Thr Asp Gly Ser Thr Ile
690                 695                 700

Glu Thr Lys Glu Thr Ala Leu Val Trp Asn Tyr Gln Phe Ala Asp Pro
705                 710                 715                 720

Asp Phe Gly Ser Cys Gln Ala Lys Glu Leu Met Glu His Leu Glu Ser
                725                 730                 735

Val Leu Thr Asn Asp Pro Val Ser Val Lys Thr Gly Gln Gln Leu Val
                740                 745                 750

Glu Val Lys Pro Gln Gly Val Asn Lys Gly Leu Val Ala Glu Arg Leu
755                 760                 765

Leu Thr Thr Met Gln Glu Lys Gly Lys Leu Leu Asp Phe Ile Leu Cys
770                 775                 780

Val Gly Asp Asp Arg Ser Asp Glu Asp Met Phe Glu Val Ile Met Ser
785                 790                 795                 800

Ala Lys Asp Gly Pro Ala Leu Ser Pro Val Ala Glu Ile Phe Ala Cys
                805                 810                 815

Thr Val Gly Gln Lys Pro Ser Lys Ala Lys Tyr Tyr Leu Asp Asp Thr
                820                 825                 830

Ala Glu Ile Ile Arg Met Leu Asp Gly Leu Ala Ala Thr Asn Thr Thr
                835                 840                 845

Ile Ser Asp Gln Thr Asp Ser Thr Ala Thr Val Pro Thr Lys Asp Leu
                850                 855                 860

Phe
865

<210> SEQ ID NO 2
<211> LENGTH: 847
<212> TYPE: PRT
<213> ORGANISM: Arabidopsis thaliana

<400> SEQUENCE: 2

Met Val Ser Arg Ser Tyr Ser Asn Leu Leu Glu Leu Ala Ser Gly Asp
1               5                   10                  15

Ser Pro Thr Phe Gly Arg Met Asn Arg Gln Ile Pro Arg Ile Met Ala
                20                  25                  30

Val Ala Gly Ile Met Ser Asn Ile Asp Asn Asp Ser Lys Asp Thr Asp
```

```
                      35                  40                  45
Leu Ser Pro Lys Asp Arg Ile Ile Val Ala Asn Glu Leu Pro Ile
 50                  55                  60

Arg Ala Gln Arg Arg Val Asp Gly Asn Gly Trp Asn Phe Ser Trp Asp
 65                  70                  75                  80

Glu Asn Ser Leu Leu Leu Gln Leu Lys Asp Gly Leu Gly Asp Glu Ala
                 85                  90                  95

Ile Glu Val Ile Tyr Val Gly Cys Leu Lys Glu Ile Pro Leu Asn
                100                 105                 110

Glu Gln Glu Glu Val Tyr Gln Ile Leu Leu Glu Ser Phe Lys Cys Val
                115                 120                 125

Pro Thr Phe Leu Pro Leu Asp Leu Tyr Thr Arg Tyr Tyr His Gly Phe
                130                 135                 140

Cys Lys Gln Gln Leu Trp Pro Leu Phe His Tyr Met Leu Pro Leu Ser
145                 150                 155                 160

Pro Asp Leu Gly Gly Arg Phe Asp Arg Thr Leu Trp Gln Ala Tyr Val
                165                 170                 175

Ser Val Asn Lys Ile Phe Ala Asp Arg Ile Met Glu Val Ile Asn Pro
                180                 185                 190

Glu Asp Asp Phe Val Trp Ile His Asp Tyr His Leu Met Val Leu Pro
                195                 200                 205

Thr Phe Leu Arg Lys Arg Phe Asn Arg Val Lys Leu Gly Phe Phe Leu
                210                 215                 220

His Ser Pro Phe Pro Ser Ser Glu Ile Tyr Lys Thr Leu Pro Ile Arg
225                 230                 235                 240

Glu Glu Leu Leu Arg Ala Leu Leu Asn Ser Asp Leu Ile Gly Phe His
                    245                 250                 255

Thr Phe Asp Tyr Ala Arg His Phe Leu Ser Cys Cys Ser Arg Met Leu
                260                 265                 270

Gly Leu Thr Tyr Glu Ser Lys Arg Gly Tyr Ile Gly Leu Glu Tyr Tyr
                275                 280                 285

Gly Arg Thr Val Ser Ile Lys Ile Leu Pro Val Gly Ile His Met Gly
290                 295                 300

Gln Leu Gln Ser Val Leu Ser Leu Pro Glu Thr Glu Arg Lys Val Gly
305                 310                 315                 320

Glu Leu Ile Glu Arg Tyr Gly Arg Lys Gly Arg Thr Met Leu Leu Gly
                    325                 330                 335

Val Asp Asp Met Asp Ile Phe Lys Gly Ile Thr Leu Lys Leu Leu Ala
                340                 345                 350

Met Glu Gln Leu Leu Met Gln His Pro Glu Trp Gln Gly Lys Val Val
                355                 360                 365

Leu Val Gln Ile Ala Asn Pro Ala Arg Gly Lys Gly Lys Asp Val Lys
                370                 375                 380

Glu Met Gln Ala Glu Thr Tyr Ser Thr Val Lys Arg Ile Asn Glu Thr
385                 390                 395                 400

Phe Gly Arg Pro Gly Tyr Asp Pro Ile Val Leu Ile Asp Ala Pro Leu
                    405                 410                 415

Lys Phe Tyr Glu Arg Val Ala Tyr Tyr Val Ala Glu Cys Cys Leu
                420                 425                 430

Val Thr Ala Val Arg Asp Gly Met Asn Leu Ile Pro Tyr Glu Tyr Ile
                435                 440                 445

Val Ser Arg Gln Gly Asn Glu Lys Leu Asp Lys Ile Leu Lys Leu Glu
                450                 455                 460
```

```
Ala Asn Asn Arg Asn Lys Lys Ser Met Leu Val Val Ser Glu Phe Ile
465                 470                 475                 480

Gly Cys Ser Pro Ser Leu Ser Gly Ala Ile Arg Val Asn Pro Trp Asn
                485                 490                 495

Val Asp Ala Val Ala Asp Ala Met Asp Ser Ala Leu Glu Val Ala Glu
            500                 505                 510

Pro Glu Lys Gln Leu Arg His Glu Lys His Tyr Lys Tyr Val Ser Thr
        515                 520                 525

His Asp Val Gly Tyr Trp Ala Arg Ser Phe Leu Gln Asp Leu Glu Arg
    530                 535                 540

Ser Cys Gly Glu His Gly Arg Arg Cys Trp Gly Ile Gly Phe Gly
545                 550                 555                 560

Leu Ser Phe Arg Val Ala Leu Asp Gln Ser Phe Arg Lys Leu Ser
                565                 570                 575

Met Glu His Ile Val Ser Ala Tyr Lys Arg Thr Lys Thr Arg Ala Ile
                580                 585                 590

Leu Leu Asp Tyr Asp Thr Leu Met Pro Gln Gly Ser Ile Asp Lys
            595                 600                 605

Arg Pro Ser Ser Lys Ser Ile Asp Ile Leu Asn Thr Leu Cys Arg Asp
610                 615                 620

Lys Gly Asn Leu Val Phe Ile Val Ser Ala Lys Ser Arg Glu Thr Leu
625                 630                 635                 640

Ser Asp Trp Phe Ser Pro Cys Glu Lys Leu Gly Ile Ala Ala Glu His
                645                 650                 655

Gly Tyr Phe Leu Arg Leu Arg Lys Ala Val Glu Trp Glu Asn Cys Val
                660                 665                 670

Ala Ala Val Asp Cys Ser Trp Lys Gln Ile Ala Glu Pro Val Met Glu
            675                 680                 685

Leu Tyr Thr Glu Thr Thr Asp Gly Ser Thr Ile Glu Asp Lys Glu Thr
        690                 695                 700

Ala Leu Val Trp Ser Tyr Glu Asp Ala Asp Pro Asp Phe Gly Ser Cys
705                 710                 715                 720

Gln Ala Lys Glu Leu Leu Asp His Leu Glu Ser Val Leu Ala Asn Glu
                725                 730                 735

Pro Val Thr Val Lys Arg Gly Gln Asn Tyr Val Glu Val Lys Pro Gln
                740                 745                 750

Gly Val Ser Lys Gly Leu Ile Ala Arg Arg Met Leu Ser Met Met Gln
            755                 760                 765

Glu Arg Gly Thr Leu Pro Glu Phe Val Leu Cys Ile Gly Asp Asp Arg
        770                 775                 780

Ser Asp Glu Asp Met Phe Glu Val Ile Cys Ser Ser Thr Glu Gly Pro
785                 790                 795                 800

Ser Ile Ala Pro Arg Ala Glu Ile Phe Ala Cys Thr Val Gly Gln Lys
                805                 810                 815

Pro Ser Lys Ala Lys Tyr Tyr Leu Asp Asp Thr Thr Glu Ile Val Arg
                820                 825                 830

Leu Met His Gly Leu Ala Ser Val Thr Asp Gln Ile Thr Pro Val
            835                 840                 845

<210> SEQ ID NO 3
<211> LENGTH: 851
<212> TYPE: PRT
<213> ORGANISM: Arabidopsis thaliana

<400> SEQUENCE: 3
```

```
Met Ile Ser Arg Ser Tyr Thr Asn Leu Leu Asp Leu Ala Ser Gly Asn
1               5                   10                  15

Phe Pro Val Met Gly Arg Glu Arg Arg Leu Pro Arg Val Met Thr
            20                  25                  30

Val Pro Gly Asn Val Ser Glu Phe Asp Glu Asp Gln Ala Tyr Ser Val
            35                  40                  45

Ser Ser Asp Asn Pro Ser Ser Val Ser Ser Asp Arg Met Ile Ile Val
        50                  55                  60

Ala Asn Arg Leu Pro Leu Lys Ala Glu Lys Arg Asn Gly Ser Trp Ser
65                  70                  75                  80

Phe Ser Trp Asp Gln Asp Ser Leu Tyr Leu Gln Leu Lys Asp Gly Leu
                85                  90                  95

Pro Glu Asp Met Glu Ile Leu Tyr Val Gly Ser Leu Ser Val Asp Val
            100                 105                 110

Asp Ser Asn Glu Gln Asp Val Ala Gln Ile Leu Leu Asp Lys Phe
        115                 120                 125

Lys Cys Val Pro Thr Phe Phe Pro Pro Asp Leu Gln Ser Lys Phe Tyr
    130                 135                 140

Asp Gly Phe Cys Lys Arg Gln Ile Trp Pro Leu Phe His Tyr Met Leu
145                 150                 155                 160

Pro Phe Ser Ala Asp His Gly Gly Arg Phe Asp Arg Ser Leu Trp Glu
                165                 170                 175

Ala Tyr Val Ala Thr Asn Lys Leu Phe Phe Gln Lys Val Ile Glu Val
            180                 185                 190

Ile Asn Pro Asp Asp Phe Val Trp Ile His Asp Tyr His Leu Met
    195                 200                 205

Val Leu Pro Thr Phe Leu Arg Arg Arg Phe Asn Arg Ile Arg Met Gly
    210                 215                 220

Phe Phe Leu His Ser Pro Phe Pro Ser Ser Glu Ile Tyr Arg Ser Leu
225                 230                 235                 240

Pro Val Arg Glu Glu Ile Leu Lys Ala Leu Leu Asn Ser Asp Leu Ile
            245                 250                 255

Gly Phe His Thr Phe Asp Tyr Ala Arg His Phe Leu Thr Cys Cys Ser
            260                 265                 270

Arg Met Leu Gly Leu Glu Tyr Gln Ser Lys Arg Gly Tyr Ile Gly Leu
            275                 280                 285

Glu Tyr Tyr Gly Arg Thr Val Gly Ile Lys Ile Met Pro Val Gly Ile
    290                 295                 300

Asn Met Gly Arg Ile Gln Ser Val Met Arg Tyr Ser Glu Glu Glu Gly
305                 310                 315                 320

Lys Val Met Glu Leu Arg Asn Arg Phe Glu Gly Lys Thr Val Leu Leu
            325                 330                 335

Gly Ile Asp Asp Met Asp Ile Phe Lys Gly Ile Asn Leu Lys Leu Leu
            340                 345                 350

Ala Met Glu Gln Met Leu Arg Gln His Pro Asn Trp Arg Gly Arg Ala
            355                 360                 365

Val Leu Val Gln Ile Val Asn Pro Ala Arg Gly Lys Gly Ile Asp Val
            370                 375                 380

Glu Glu Ile Arg Gly Glu Ile Glu Glu Ser Cys Arg Arg Ile Asn Gly
385                 390                 395                 400

Glu Phe Gly Lys Pro Gly Tyr Gln Pro Ile Ile Tyr Ile Asp Thr Pro
            405                 410                 415

Val Ser Ile Asn Glu Ile Asn Ala Tyr Tyr His Ile Ala Glu Cys Val
            420                 425                 430
```

```
Val Val Thr Ala Val Arg Asp Gly Met Asn Leu Thr Pro Tyr Glu Tyr
            435                 440                 445
Ile Val Cys Arg Gln Gly Leu Leu Gly Ser Glu Ser Asp Phe Ser Gly
        450                 455                 460
Pro Lys Lys Ser Met Leu Val Ala Ser Glu Phe Ile Gly Cys Ser Pro
465                 470                 475                 480
Ser Leu Ser Gly Ala Ile Arg Val Asn Pro Trp Asn Val Glu Ala Thr
                485                 490                 495
Gly Glu Ala Leu Asn Glu Ala Leu Ser Met Ser Asp Ala Glu Lys Gln
            500                 505                 510
Leu Arg His Glu Lys His Phe Arg Tyr Val Ser Thr His Asp Val Ala
        515                 520                 525
Tyr Trp Ser Arg Ser Phe Leu Gln Asp Leu Glu Arg Ile Cys Val Asp
        530                 535                 540
His Phe Lys Lys Arg Cys Trp Gly Met Gly Ile Ser Phe Gly Phe Arg
545                 550                 555                 560
Val Val Ala Leu Asp Pro Asn Phe Arg Lys Leu Ser Ile Pro Cys Ile
                565                 570                 575
Val Ser Asp Tyr Lys Arg Ala Lys Ser Arg Ala Ile Leu Leu Asp Tyr
            580                 585                 590
Asp Gly Thr Leu Met Pro Gln Asn Ser Ile Asn Lys Ala Pro Ser Gln
        595                 600                 605
Glu Val Leu Asn Phe Leu Asp Ala Leu Cys Glu Asp Lys Lys Asn Ser
        610                 615                 620
Ile Phe Ile Val Ser Gly Arg Gly Arg Glu Ser Leu Ser Lys Trp Phe
625                 630                 635                 640
Thr Pro Cys Lys Lys Ile Gly Ile Ala Ala His Gly Tyr Phe Leu
                645                 650                 655
Lys Trp Ser Gly Ser Glu Glu Trp Glu Thr Cys Gly Gln Ser Ser Asp
            660                 665                 670
Phe Gly Trp Met Gln Ile Val Glu Pro Val Met Lys Gln Tyr Thr Glu
        675                 680                 685
Ser Thr Asp Gly Ser Ser Ile Glu Ile Lys Glu Ser Ala Leu Val Trp
        690                 695                 700
Gln Tyr Arg Asp Ala Asp Pro Gly Phe Gly Ser Leu Gln Ala Lys Glu
705                 710                 715                 720
Met Leu Glu His Leu Glu Ser Val Leu Ala Asn Glu Pro Val Ala Val
                725                 730                 735
Lys Ser Gly His Tyr Ile Val Glu Val Lys Pro Gln Gly Val Ser Lys
            740                 745                 750
Gly Ser Val Ser Glu Lys Ile Phe Ser Ser Met Ala Gly Lys Gly Lys
        755                 760                 765
Pro Val Asp Phe Val Leu Cys Ile Gly Asp Asp Arg Ser Asp Glu Asp
770                 775                 780
Met Phe Glu Ala Ile Gly Asn Ala Met Ser Lys Arg Leu Leu Cys Asp
785                 790                 795                 800
Asn Ala Leu Val Phe Ala Cys Thr Val Gly Gln Lys Pro Ser Lys Ala
                805                 810                 815
Lys Tyr Tyr Leu Asp Asp Thr Thr Glu Val Thr Cys Met Leu Glu Ser
            820                 825                 830
Leu Ala Glu Ala Ser Glu Ala Ser Asn Phe Ser Met Arg Glu Leu Asp
        835                 840                 845
Glu Ala Leu
```

-continued

850

<210> SEQ ID NO 4
<211> LENGTH: 826
<212> TYPE: PRT
<213> ORGANISM: Arabidopsis thaliana

<400> SEQUENCE: 4

Met Thr Val Pro Gly Ile Ile Thr Asp Val Asp Gly Asp Thr Thr Ser
1               5                   10                  15

Glu Val Thr Ser Thr Ser Gly Gly Ser Arg Glu Arg Lys Ile Ile Val
            20                  25                  30

Ala Asn Met Leu Pro Leu Gln Ser Lys Arg Asp Ala Glu Thr Gly Lys
        35                  40                  45

Trp Cys Phe Asn Trp Asp Glu Ser Leu Gln Leu Gln Leu Arg Asp
    50                  55                  60

Gly Phe Ser Ser Glu Thr Glu Phe Leu Tyr Val Gly Ser Leu Asn Val
65                  70                  75                  80

Asp Ile Glu Thr Asn Glu Gln Glu Val Ser Gln Lys Leu Leu Glu
                85                  90                  95

Glu Phe Asn Cys Val Ala Thr Phe Leu Ser Gln Glu Leu Gln Glu Met
            100                 105                 110

Phe Tyr Leu Gly Phe Cys Lys His Gln Leu Trp Pro Leu Phe His Tyr
        115                 120                 125

Met Leu Pro Met Phe Pro Asp His Gly Asp Arg Phe Asp Arg Arg Leu
    130                 135                 140

Trp Gln Ala Tyr Val Ser Ala Asn Lys Ile Phe Ser Asp Arg Val Met
145                 150                 155                 160

Glu Val Ile Asn Pro Glu Asp Asp Tyr Val Trp Ile Gln Asp Tyr His
                165                 170                 175

Leu Met Val Leu Pro Thr Phe Leu Arg Lys Arg Phe Asn Arg Ile Lys
            180                 185                 190

Leu Gly Phe Phe Leu His Ser Pro Phe Pro Ser Ser Glu Ile Tyr Arg
        195                 200                 205

Thr Leu Pro Val Arg Asp Glu Ile Leu Arg Gly Leu Leu Asn Cys Asp
    210                 215                 220

Leu Ile Gly Phe His Thr Phe Asp Tyr Ala Arg His Phe Leu Ser Cys
225                 230                 235                 240

Cys Ser Arg Met Leu Gly Leu Asp Tyr Glu Ser Lys Arg Gly His Ile
                245                 250                 255

Gly Leu Asp Tyr Phe Gly Arg Thr Val Tyr Ile Lys Ile Leu Pro Val
            260                 265                 270

Gly Val His Met Gly Arg Leu Glu Ser Val Leu Ser Leu Asp Ser Thr
        275                 280                 285

Ala Ala Lys Thr Lys Glu Ile Gln Glu Gln Phe Lys Gly Lys Lys Leu
    290                 295                 300

Val Leu Gly Ile Asp Asp Met Asp Ile Phe Lys Gly Ile Ser Leu Lys
305                 310                 315                 320

Leu Ile Ala Met Glu His Leu Phe Glu Thr Tyr Trp His Leu Lys Gly
                325                 330                 335

Lys Val Val Leu Val Gln Ile Val Asn Pro Ala Arg Ser Ser Gly Lys
            340                 345                 350

Asp Val Glu Glu Ala Lys Arg Glu Thr Tyr Glu Thr Ala Arg Arg Ile
        355                 360                 365

Asn Glu Arg Tyr Gly Thr Ser Asp Tyr Lys Pro Ile Val Leu Ile Asp

```
            370                 375                 380
Arg Leu Val Pro Arg Ser Glu Lys Thr Ala Tyr Tyr Ala Ala Ala Asp
385                 390                 395                 400

Cys Cys Leu Val Asn Ala Val Arg Asp Gly Met Asn Leu Val Pro Tyr
                405                 410                 415

Lys Tyr Ile Val Cys Arg Gln Gly Thr Arg Ser Asn Lys Ala Val Val
                420                 425                 430

Asp Ser Ser Pro Arg Thr Ser Thr Leu Val Val Ser Glu Phe Ile Gly
                435                 440                 445

Cys Ser Pro Ser Leu Ser Gly Ala Ile Arg Val Asn Pro Trp Asp Val
450                 455                 460

Asp Ala Val Ala Glu Ala Val Asn Ser Ala Leu Lys Met Ser Glu Thr
465                 470                 475                 480

Glu Lys Gln Leu Arg His Glu Lys His Tyr His Tyr Ile Ser Thr His
                485                 490                 495

Asp Val Gly Tyr Trp Ala Lys Ser Phe Met Gln Asp Leu Glu Arg Ala
                500                 505                 510

Cys Arg Asp His Tyr Ser Lys Arg Cys Trp Gly Ile Gly Phe Gly Leu
                515                 520                 525

Gly Phe Arg Val Leu Ser Leu Ser Pro Ser Phe Arg Lys Leu Ser Val
530                 535                 540

Glu His Ile Val Pro Val Tyr Arg Lys Thr Gln Arg Arg Ala Ile Phe
545                 550                 555                 560

Leu Asp Tyr Asp Gly Thr Leu Val Pro Glu Ser Ser Ile Val Gln Asp
                565                 570                 575

Pro Ser Asn Glu Val Val Ser Val Leu Lys Ala Leu Cys Glu Asp Pro
                580                 585                 590

Asn Asn Thr Val Phe Ile Val Ser Gly Arg Gly Arg Glu Ser Leu Ser
                595                 600                 605

Asn Trp Leu Ser Pro Cys Glu Asn Leu Gly Ile Ala Ala Glu His Gly
                610                 615                 620

Tyr Phe Ile Arg Trp Lys Ser Lys Asp Glu Trp Glu Thr Cys Tyr Ser
625                 630                 635                 640

Pro Thr Asp Thr Glu Trp Arg Ser Met Val Glu Pro Val Met Arg Ser
                645                 650                 655

Tyr Met Glu Ala Thr Asp Gly Thr Ser Ile Glu Phe Lys Glu Ser Ala
                660                 665                 670

Leu Val Trp His His Gln Asp Ala Asp Pro Asp Phe Gly Ser Cys Gln
                675                 680                 685

Ala Lys Glu Met Leu Asp His Leu Glu Ser Val Leu Ala Asn Glu Pro
690                 695                 700

Val Val Val Lys Arg Gly Gln His Ile Val Glu Val Lys Pro Gln Gly
705                 710                 715                 720

Val Ser Lys Gly Leu Ala Ala Glu Lys Val Ile Arg Glu Met Val Glu
                725                 730                 735

Arg Gly Glu Pro Pro Glu Met Val Met Cys Ile Gly Asp Asp Arg Ser
                740                 745                 750

Asp Glu Asp Met Phe Glu Ser Ile Leu Ser Thr Val Thr Asn Pro Glu
                755                 760                 765

Leu Leu Val Gln Pro Glu Val Phe Ala Cys Thr Val Gly Arg Lys Pro
                770                 775                 780

Ser Lys Ala Lys Tyr Phe Leu Asp Asp Glu Ala Asp Val Leu Lys Leu
785                 790                 795                 800
```

-continued

```
Leu Arg Gly Leu Gly Asp Ser Ser Ser Leu Lys Pro Ser Ser Ser
                805                 810                 815

His Thr Gln Val Ala Phe Glu Ser Ile Val
            820                 825

<210> SEQ ID NO 5
<211> LENGTH: 867
<212> TYPE: PRT
<213> ORGANISM: Arabidopsis thaliana

<400> SEQUENCE: 5

Met Val Ser Arg Ser Cys Ala Asn Phe Leu Asp Leu Ala Ser Trp Asp
1               5                   10                  15

Leu Leu Asp Phe Pro Gln Thr Gln Arg Ala Leu Pro Arg Val Met Thr
            20                  25                  30

Val Pro Gly Ile Ile Ser Glu Leu Asp Gly Gly Tyr Ser Asp Gly Ser
        35                  40                  45

Ser Asp Val Asn Ser Ser Asn Ser Ser Arg Glu Arg Lys Ile Ile Val
    50                  55                  60

Ala Asn Met Leu Pro Leu Gln Ala Lys Arg Asp Thr Glu Thr Gly Gln
65                  70                  75                  80

Trp Cys Phe Ser Trp Asp Glu Asp Ser Leu Leu Gln Leu Arg Asp
                85                  90                  95

Gly Phe Ser Ser Asp Thr Glu Phe Val Tyr Ile Gly Ser Leu Asn Ala
            100                 105                 110

Asp Ile Gly Ile Ser Glu Gln Glu Val Ser His Lys Leu Leu Leu
        115                 120                 125

Asp Phe Asn Cys Val Pro Thr Phe Leu Pro Lys Glu Met Gln Glu Lys
130                 135                 140

Phe Tyr Leu Gly Phe Cys Lys His His Leu Trp Pro Leu Phe His Tyr
145                 150                 155                 160

Met Leu Pro Met Phe Pro Asp His Gly Asp Arg Phe Asp Arg Arg Leu
                165                 170                 175

Trp Gln Ala Tyr Val Ser Ala Asn Lys Ile Phe Ser Asp Arg Val Met
            180                 185                 190

Glu Val Ile Asn Pro Glu Glu Asp Tyr Val Trp Ile His Asp Tyr His
        195                 200                 205

Leu Met Val Leu Pro Thr Phe Leu Arg Lys Arg Phe Asn Arg Ile Lys
210                 215                 220

Leu Gly Phe Phe Leu His Ser Pro Phe Pro Ser Ser Glu Ile Tyr Arg
225                 230                 235                 240

Thr Leu Pro Val Arg Asp Asp Leu Leu Arg Gly Leu Leu Asn Cys Asp
                245                 250                 255

Leu Ile Gly Phe His Thr Phe Asp Tyr Ala Arg His Phe Leu Ser Cys
            260                 265                 270

Cys Ser Arg Met Leu Gly Leu Asp Tyr Glu Ser Lys Arg Gly His Ile
        275                 280                 285

Gly Leu Asp Tyr Phe Gly Arg Thr Val Phe Ile Lys Ile Leu Pro Val
290                 295                 300

Gly Ile His Met Gly Arg Leu Glu Ser Val Leu Asn Leu Pro Ser Thr
305                 310                 315                 320

Ala Ala Lys Met Lys Glu Ile Gln Glu Gln Phe Lys Gly Lys Lys Leu
                325                 330                 335

Ile Leu Gly Val Asp Asp Met Asp Ile Phe Lys Gly Ile Ser Leu Lys
            340                 345                 350
```

```
Leu Ile Ala Met Glu Arg Leu Phe Glu Thr Tyr Trp His Met Arg Gly
            355                 360                 365

Lys Leu Val Leu Ile Gln Ile Val Asn Pro Ala Arg Ala Thr Gly Lys
        370                 375                 380

Asp Val Glu Ala Lys Lys Glu Thr Tyr Ser Thr Ala Lys Arg Ile
385                 390                 395                 400

Asn Glu Arg Tyr Gly Ser Ala Gly Tyr Gln Pro Val Ile Leu Ile Asp
                405                 410                 415

Arg Leu Val Pro Arg Tyr Glu Lys Thr Ala Tyr Tyr Ala Met Ala Asp
                420                 425                 430

Cys Cys Leu Val Asn Ala Val Arg Asp Gly Met Asn Leu Val Pro Tyr
            435                 440                 445

Lys Tyr Ile Ile Cys Arg Gln Gly Thr Pro Gly Met Asp Lys Ala Met
        450                 455                 460

Gly Ile Ser His Asp Ser Ala Arg Thr Ser Met Leu Val Val Ser Glu
465                 470                 475                 480

Phe Ile Gly Cys Ser Pro Ser Leu Ser Gly Ala Ile Arg Val Asn Pro
                485                 490                 495

Trp Asp Val Asp Ala Val Ala Glu Ala Val Asn Leu Ala Leu Thr Met
            500                 505                 510

Gly Glu Thr Glu Lys Arg Leu Arg His Glu Lys His Tyr His Tyr Val
        515                 520                 525

Ser Thr His Asp Val Gly Tyr Trp Ala Lys Ser Phe Met Gln Asp Leu
        530                 535                 540

Glu Arg Ala Cys Arg Glu His Tyr Asn Lys Arg Cys Trp Gly Ile Gly
545                 550                 555                 560

Phe Gly Leu Ser Phe Arg Val Leu Ser Leu Ser Pro Ser Phe Arg Lys
                565                 570                 575

Leu Ser Ile Asp His Ile Val Ser Thr Tyr Arg Asn Thr Gln Arg Arg
                580                 585                 590

Ala Ile Phe Leu Asp Tyr Asp Gly Thr Leu Val Pro Glu Ser Ser Ile
            595                 600                 605

Ile Lys Thr Pro Asn Ala Glu Val Leu Ser Val Leu Lys Ser Leu Cys
        610                 615                 620

Gly Asp Pro Lys Asn Thr Val Phe Val Val Ser Gly Arg Gly Trp Glu
625                 630                 635                 640

Ser Leu Ser Asp Trp Leu Ser Pro Cys Glu Asn Leu Gly Ile Ala Ala
                645                 650                 655

Glu His Gly Tyr Phe Ile Arg Trp Ser Ser Lys Lys Glu Trp Glu Thr
                660                 665                 670

Cys Tyr Ser Ser Ala Glu Ala Glu Trp Lys Thr Met Val Glu Pro Val
            675                 680                 685

Met Arg Ser Tyr Met Asp Ala Thr Asp Gly Ser Thr Ile Glu Tyr Lys
        690                 695                 700

Glu Ser Ala Leu Val Trp His His Gln Asp Ala Asp Pro Asp Phe Gly
705                 710                 715                 720

Ala Cys Gln Ala Lys Glu Leu Leu Asp His Leu Glu Ser Val Leu Ala
                725                 730                 735

Asn Glu Pro Val Val Val Lys Arg Gly Gln His Ile Val Glu Val Lys
                740                 745                 750

Pro Gln Gly Val Ser Lys Gly Leu Ala Val Glu Lys Val Ile His Gln
            755                 760                 765

Met Val Glu Asp Gly Asn Pro Pro Asp Met Val Met Cys Ile Gly Asp
        770                 775                 780
```

```
Asp Arg Ser Asp Glu Asp Met Phe Glu Ser Ile Leu Ser Thr Val Thr
785                 790                 795                 800

Asn Pro Asp Leu Pro Met Pro Pro Glu Ile Phe Ala Cys Thr Val Gly
            805                 810                 815

Arg Lys Pro Ser Lys Ala Lys Tyr Phe Leu Asp Asp Val Ser Asp Val
            820                 825                 830

Leu Lys Leu Leu Gly Gly Leu Ala Ala Ala Thr Ser Ser Ser Lys Pro
            835                 840                 845

Glu Tyr Gln Gln Gln Ser Ser Ser Leu His Thr Gln Val Ala Phe Glu
            850                 855                 860

Ser Ile Ile
865

<210> SEQ ID NO 6
<211> LENGTH: 861
<212> TYPE: PRT
<213> ORGANISM: Arabidopsis thaliana

<400> SEQUENCE: 6

Met Gly Ser Lys Ser Phe Gly Asn Leu Leu Asp Leu Ala Ser Gly Asp
1               5                   10                  15

Leu Leu Asp Ile Pro Gln Thr Pro Arg Tyr Leu Pro Arg Val Met Thr
            20                  25                  30

Val Pro Gly Ile Ile Ser Asp Val Asp Gly Tyr Gly Ile Ser Asp Gly
            35                  40                  45

Asp Ser Asp Val Ile Ser Leu Pro Cys Arg Glu Arg Lys Ile Ile Val
        50                  55                  60

Ala Asn Phe Leu Pro Leu Asn Gly Lys Lys Asp Ser Glu Thr Gly Lys
65                  70                  75                  80

Trp Lys Phe Ser Leu Asp Asn Asp Ser Pro Leu Leu His Leu Lys Asp
                85                  90                  95

Gly Phe Ser Pro Glu Thr Glu Val Ile Tyr Val Gly Ser Leu Lys Thr
            100                 105                 110

His Val Asp Val Ser Glu Gln Asp Glu Val Ser His Asn Leu Phe Glu
            115                 120                 125

Glu Phe Asn Cys Val Ala Thr Phe Leu Pro Gln Asp Val His Lys Lys
        130                 135                 140

Phe Tyr Leu Gly Phe Cys Lys Gln Gln Leu Trp Pro Leu Phe His Tyr
145                 150                 155                 160

Met Leu Pro Met Cys Pro Asp His Gly Glu Arg Phe Asp Arg Gly Leu
                165                 170                 175

Trp Gln Ala Tyr Val Ser Ala Asn Lys Ile Phe Ala Asp Lys Val Met
            180                 185                 190

Gly Val Ile Asn Leu Glu Glu Asp Tyr Ile Trp Ile His Asp Tyr His
            195                 200                 205

Leu Met Val Leu Pro Thr Phe Leu Arg Arg Arg Phe His Arg Val Lys
        210                 215                 220

Leu Gly Phe Phe Leu His Ser Pro Phe Pro Ser Ser Glu Ile Tyr Arg
225                 230                 235                 240

Thr Leu Pro Val Arg Glu Glu Leu Leu Arg Gly Leu Leu Asn Cys Asp
                245                 250                 255

Leu Ile Gly Phe His Thr Phe Asp Tyr Ala Arg His Phe Leu Ser Cys
            260                 265                 270

Cys Cys Arg Met Leu Gly Leu Glu Tyr Glu Ser Lys Arg Gly His Ile
            275                 280                 285
```

```
Ala Leu Asp Tyr Leu Gly Arg Thr Val Phe Leu Lys Ile Leu Pro Ile
    290                 295                 300

Gly Ile His Met Gly Arg Leu Glu Ser Val Leu Asn Leu Pro Ala Thr
305                 310                 315                 320

Ala Glu Lys Leu Lys Glu Ile Gln Glu Lys Tyr Arg Gly Lys Lys Ile
                325                 330                 335

Ile Leu Gly Val Asp Asp Met Asp Ile Phe Lys Gly Leu Ser Leu Lys
                340                 345                 350

Ile Leu Ala Phe Glu His Leu Gln Gln Tyr Pro Ser Met Leu Gly
            355                 360                 365

Lys Ile Val Leu Ile Gln Ile Val Asn Pro Ala Arg Gly Ser Gly Lys
    370                 375                 380

Asp Val Gln Glu Ala Arg Lys Glu Thr Tyr Asp Thr Val Lys Arg Ile
385                 390                 395                 400

Asn Glu Arg Tyr Gly Ser His Asp Tyr Glu Pro Val Val Leu Ile Asp
                405                 410                 415

Arg Pro Val Pro Arg Phe Glu Lys Ser Ala Tyr Tyr Ala Leu Ala Glu
            420                 425                 430

Cys Cys Ile Val Asn Ala Val Arg Asp Gly Met Asn Leu Val Pro Tyr
            435                 440                 445

Lys Tyr Thr Val Cys Arg Gln Gly Thr Pro Ser Met Asn Lys Ser Leu
    450                 455                 460

Gly Val Ser Asp Asp Leu Pro Arg Thr Ser Thr Leu Val Leu Ser Glu
465                 470                 475                 480

Phe Ile Gly Cys Ser Pro Ser Leu Ser Gly Ala Ile Arg Val Asn Pro
                485                 490                 495

Trp Asp Val Asp Ala Val Ala Asp Ser Leu Tyr Ser Ala Ile Thr Met
            500                 505                 510

Ser Asp Phe Glu Lys Gln Leu Arg His Lys Lys His Phe His Tyr Ile
    515                 520                 525

Ser Thr His Asp Val Gly Tyr Trp Ala Arg Ser Phe Ser Gln Asp Leu
530                 535                 540

Glu Arg Ala Ser Arg Asp His Tyr Ser Lys Arg Cys Trp Gly Val Gly
545                 550                 555                 560

Trp Gly Leu Gly Phe Arg Leu Val Ala Leu Ser Pro Asn Phe Arg Arg
                565                 570                 575

Leu Ser Ile Glu Gln Thr Val Ser Ala Tyr Arg Arg Ser Ser Lys Arg
            580                 585                 590

Ala Ile Phe Leu Asp Tyr Asp Gly Thr Leu Val Pro Glu Thr Ser Ile
            595                 600                 605

Val Lys Asp Pro Ser Ala Glu Val Ile Ser Ala Leu Lys Ala Leu Cys
    610                 615                 620

Ser Asp Pro Asn Asn Thr Ile Phe Ile Val Ser Gly Arg Gly Lys Val
625                 630                 635                 640

Ser Leu Ser Glu Trp Leu Ala Pro Cys Glu Asn Leu Gly Ile Ala Ala
                645                 650                 655

Glu His Gly Tyr Phe Thr Arg Trp Asn Lys Ser Ser Asp Trp Glu Thr
            660                 665                 670

Ser Gly Leu Ser Asp Asp Leu Glu Trp Lys Lys Val Val Glu Pro Ile
            675                 680                 685

Met Arg Leu Tyr Thr Glu Thr Thr Asp Gly Ser Asn Ile Glu Ala Lys
    690                 695                 700

Glu Ser Ala Leu Val Trp His His Gln Asp Ala Asp Pro Asp Phe Gly
```

-continued

```
                705                 710                 715                 720
Ser Cys Gln Ala Lys Glu Leu Leu Asp His Leu Glu Thr Val Leu Val
                    725                 730                 735

Asn Glu Pro Val Ile Val Asn Arg Gly His Gln Ile Val Glu Val Lys
            740                 745                 750

Pro Gln Gly Val Ser Lys Gly Leu Val Thr Gly Lys Ile Leu Ser Arg
        755                 760                 765

Met Leu Glu Asp Gly Ile Ala Pro Asp Phe Val Val Cys Ile Gly Asp
    770                 775                 780

Asp Arg Ser Asp Glu Glu Met Phe Glu Asn Ile Ser Thr Thr Leu Ser
785                 790                 795                 800

Ala Gln Ser Ser Ser Met Ser Thr Glu Ile Phe Ala Cys Thr Val Gly
                805                 810                 815

Arg Lys Pro Ser Lys Ala Lys Tyr Phe Leu Asp Glu Val Ser Asp Val
            820                 825                 830

Val Lys Leu Leu Gln Gly Leu Ala Asn Thr Ser Ser Pro Lys Pro Arg
        835                 840                 845

Tyr Pro Ser His Leu Arg Val Ser Phe Glu Ser Val Val
    850                 855                 860

<210> SEQ ID NO 7
<211> LENGTH: 862
<212> TYPE: PRT
<213> ORGANISM: Arabidopsis thaliana

<400> SEQUENCE: 7

Met Ser Pro Glu Ser Trp Lys Asp Gln Leu Ser Leu Val Ser Ala Asp
1               5                   10                  15

Asp Tyr Arg Ile Met Gly Arg Asn Arg Ile Pro Asn Ala Val Thr Lys
            20                  25                  30

Leu Ser Gly Leu Glu Thr Asp Asp Pro Asn Gly Gly Ala Trp Val Thr
        35                  40                  45

Lys Pro Lys Arg Ile Val Val Ser Asn Gln Leu Pro Leu Arg Ala His
    50                  55                  60

Arg Asp Ile Ser Ser Asn Lys Trp Cys Phe Glu Phe Asp Asn Asp Ser
65                  70                  75                  80

Leu Tyr Leu Gln Leu Lys Asp Gly Phe Pro Pro Glu Thr Glu Val Val
                85                  90                  95

Tyr Val Gly Ser Leu Asn Ala Asp Val Leu Pro Ser Glu Gln Glu Asp
            100                 105                 110

Val Ser Gln Phe Leu Leu Glu Lys Phe Gln Cys Val Pro Thr Phe Leu
        115                 120                 125

Pro Ser Asp Leu Leu Asn Lys Tyr Tyr His Gly Phe Cys Lys His Tyr
    130                 135                 140

Leu Trp Pro Ile Phe His Tyr Leu Leu Pro Met Thr Gln Ala Gln Gly
145                 150                 155                 160

Ser Leu Phe Asp Arg Ser Asn Trp Arg Ala Tyr Thr Thr Val Asn Lys
                165                 170                 175

Ile Phe Ala Asp Lys Ile Phe Glu Val Leu Asn Pro Asp Asp Asp Tyr
            180                 185                 190

Val Trp Ile His Asp Tyr His Leu Met Ile Leu Pro Thr Phe Leu Arg
        195                 200                 205

Asn Arg Phe His Arg Ile Lys Leu Gly Ile Phe Leu His Ser Pro Phe
    210                 215                 220

Pro Ser Ser Glu Ile Tyr Arg Thr Leu Pro Val Arg Asp Glu Ile Leu
```

```
            225                 230                 235                 240
Lys Gly Phe Leu Asn Cys Asp Leu Val Gly Phe His Thr Phe Asp Tyr
                245                 250                 255
Ala Arg His Phe Leu Ser Cys Cys Ser Arg Met Leu Gly Leu Asp Tyr
                260                 265                 270
Glu Ser Lys Arg Gly Tyr Ile Gly Leu Glu Tyr Phe Gly Arg Thr Val
                275                 280                 285
Ser Ile Lys Ile Leu Pro Val Gly Ile His Met Gly Gln Ile Glu Ser
                290                 295                 300
Ile Lys Ala Ser Glu Lys Thr Ala Glu Lys Val Lys Arg Leu Arg Glu
305                 310                 315                 320
Arg Phe Lys Gly Asn Ile Val Met Leu Gly Val Asp Asp Leu Asp Met
                325                 330                 335
Phe Lys Gly Ile Ser Leu Lys Phe Trp Ala Met Gly Gln Leu Leu Glu
                340                 345                 350
Gln Asn Glu Glu Leu Arg Gly Lys Val Val Leu Val Gln Ile Thr Asn
                355                 360                 365
Pro Ala Arg Ser Ser Gly Lys Asp Val Gln Asp Val Glu Lys Gln Ile
                370                 375                 380
Asn Leu Ile Ala Asp Glu Ile Asn Ser Lys Phe Gly Arg Pro Gly Gly
385                 390                 395                 400
Tyr Lys Pro Ile Val Phe Ile Asn Gly Pro Val Ser Thr Leu Asp Lys
                405                 410                 415
Val Ala Tyr Tyr Ala Ile Ser Glu Cys Val Val Asn Ala Val Arg
                420                 425                 430
Asp Gly Met Asn Leu Val Pro Tyr Lys Tyr Thr Val Thr Arg Gln Gly
                435                 440                 445
Ser Pro Ala Leu Asp Ala Ala Leu Gly Phe Gly Glu Asp Asp Val Arg
                450                 455                 460
Lys Ser Val Ile Ile Val Ser Glu Phe Ile Gly Cys Ser Pro Ser Leu
465                 470                 475                 480
Ser Gly Ala Ile Arg Val Asn Pro Trp Asn Ile Asp Ala Val Thr Asn
                485                 490                 495
Ala Met Ser Ser Ala Met Thr Met Ser Asp Lys Glu Lys Asn Leu Arg
                500                 505                 510
His Gln Lys His His Lys Tyr Ile Ser Ser His Asn Val Ala Tyr Trp
                515                 520                 525
Ala Arg Ser Tyr Asp Gln Asp Leu Gln Arg Ala Cys Lys Asp His Tyr
                530                 535                 540
Asn Lys Arg Phe Trp Gly Val Gly Phe Gly Leu Phe Lys Val Val
545                 550                 555                 560
Ala Leu Asp Pro Asn Phe Arg Arg Leu Cys Gly Glu Thr Ile Val Pro
                565                 570                 575
Ala Tyr Arg Arg Ser Ser Arg Leu Ile Leu Asp Tyr Asp Gly
                580                 585                 590
Thr Met Met Asp Gln Asp Thr Leu Asp Lys Arg Pro Ser Asp Asp Leu
                595                 600                 605
Ile Ser Leu Leu Asn Arg Leu Cys Asp Asp Pro Ser Asn Leu Val Phe
                610                 615                 620
Ile Val Ser Gly Arg Gly Lys Asp Pro Leu Ser Lys Trp Phe Asp Ser
625                 630                 635                 640
Cys Pro Asn Leu Gly Ile Ser Ala Glu His Gly Tyr Phe Thr Arg Trp
                645                 650                 655
```

```
Asn Ser Asn Ser Pro Trp Glu Thr Ser Glu Leu Pro Ala Asp Leu Ser
            660                 665                 670

Trp Lys Lys Ile Ala Lys Pro Val Met Asn His Tyr Met Glu Ala Thr
        675                 680                 685

Asp Gly Ser Phe Ile Glu Glu Lys Glu Ser Ala Met Val Trp His His
    690                 695                 700

Gln Glu Ala Asp His Ser Phe Gly Ser Trp Gln Ala Lys Glu Leu Leu
705                 710                 715                 720

Asp His Leu Glu Ser Val Leu Thr Asn Glu Pro Val Val Lys Arg
                725                 730                 735

Gly Gln His Ile Val Glu Val Lys Pro Gln Gly Val Ser Lys Gly Lys
                740                 745                 750

Val Val Glu His Leu Ile Ala Thr Met Arg Asn Thr Lys Gly Lys Arg
                755                 760                 765

Pro Asp Phe Leu Leu Cys Ile Gly Asp Asp Arg Ser Asp Glu Asp Met
    770                 775                 780

Phe Asp Ser Ile Val Lys His Gln Asp Val Ser Ser Ile Gly Leu Glu
785                 790                 795                 800

Glu Val Phe Ala Cys Thr Val Gly Gln Lys Pro Ser Lys Ala Lys Tyr
                805                 810                 815

Tyr Leu Asp Asp Thr Pro Ser Val Ile Lys Met Leu Glu Trp Leu Ala
            820                 825                 830

Ser Ala Ser Asp Gly Ser Lys His Glu Gln Gln Lys Lys Gln Ser Lys
            835                 840                 845

Phe Thr Phe Gln Gln Pro Met Gly Gln Cys Arg Lys Lys Ala
    850                 855                 860

<210> SEQ ID NO 8
<211> LENGTH: 862
<212> TYPE: PRT
<213> ORGANISM: Oryza sativa

<400> SEQUENCE: 8

Met Val Ser Lys Ser Tyr Ser Asn Leu Leu Glu Met Ser Cys Gly Asp
1               5                   10                  15

Gly Val Asp Phe Arg Gln Pro Phe Lys Ser Leu Pro Arg Val Val Thr
            20                  25                  30

Ser Pro Gly Ile Ile Ser Asp Pro Asp Trp Asp Thr Arg Ser Asp Gly
        35                  40                  45

Asp Ser Val Gly Ser Ala Ser Ser Val Glu Arg Lys Ile Ile Val Ala
    50                  55                  60

Asn Phe Leu Pro Leu Asn Cys Thr Lys Asp Glu Ala Gly Gln Trp Ser
65                  70                  75                  80

Phe Ser Arg Asp Asp Asp Ala Leu Leu Met Gln Leu Lys Asp Gly Phe
                85                  90                  95

Ser Asn Glu Thr Asp Val Ile Tyr Val Gly Ser Leu Lys Val Gln Val
            100                 105                 110

Asp Pro Ser Glu Gln Asp Gln Val Ala Gln Lys Leu Leu Arg Asp Tyr
        115                 120                 125

Arg Cys Ile Pro Thr Phe Leu Pro Asp Leu Gln Gln Gln Phe Tyr
    130                 135                 140

His Gly Phe Cys Lys Gln Gln Leu Trp Pro Leu Phe His Tyr Met Leu
145                 150                 155                 160

Pro Ile Cys Leu Asp Lys Gly Glu Leu Phe Asp Arg Ser Leu Phe Gln
                165                 170                 175
```

```
Ala Tyr Val Arg Ala Asn Lys Leu Phe Ala Asp Lys Val Met Glu Ala
            180                 185                 190

Ile Asn Thr Asp Asp His Val Trp Val His Asp Tyr His Leu Met
            195                 200                 205

Leu Leu Pro Thr Phe Leu Arg Lys Arg Leu His Arg Ile Lys Leu Gly
210                 215                 220

Phe Phe Leu His Ser Pro Phe Pro Ser Ser Glu Ile Tyr Arg Ser Leu
225                 230                 235                 240

Pro Val Arg Asp Glu Ile Leu Lys Ser Leu Leu Asn Ala Asp Leu Ile
            245                 250                 255

Gly Phe Gln Thr Phe Asp Tyr Ala Arg His Phe Leu Ser Cys Cys Ser
            260                 265                 270

Arg Leu Leu Gly Leu His Tyr Glu Ser Lys Arg Gly Tyr Ile Gly Ile
            275                 280                 285

Asp Tyr Phe Gly Arg Thr Val Ser Leu Lys Ile Leu Ser Val Gly Val
            290                 295                 300

His Val Gly Arg Leu Glu Ser Ile Leu Lys Leu Pro Ala Thr Val Lys
305                 310                 315                 320

Lys Val Gln Glu Ile Glu Gln Arg Tyr Lys Gly Lys Met Leu Met Leu
            325                 330                 335

Gly Val Asp Asp Met Asp Ile Phe Lys Gly Ile Ser Leu Lys Leu Leu
            340                 345                 350

Gly Leu Glu Leu Leu Asp Arg Asn Pro Lys Leu Arg Gly Lys Val
            355                 360                 365

Val Leu Val Gln Ile Val Asn Pro Ala Arg Ser Thr Gly Lys Asp Val
            370                 375                 380

Glu Glu Ala Ile Thr Glu Ser Val Ser Val Ala Glu Arg Ile Asn Leu
385                 390                 395                 400

Lys Tyr Gly Ser Val Asp Tyr Lys Pro Val Val Leu Ile Asp His Arg
            405                 410                 415

Ile Pro Phe Tyr Glu Lys Ile Ala Phe Tyr Ala Ala Ser Asp Cys Cys
            420                 425                 430

Ile Val Asn Ala Leu Arg Asp Gly Met Asn Leu Val Pro Tyr Glu Tyr
            435                 440                 445

Thr Val Cys Arg Gln Gly Asn Glu Glu Ile Asp Asn Ala Arg Gly Ser
450                 455                 460

Asp Thr Asn Cys His His Thr Ser Thr Leu Ile Val Ser Glu Phe Val
465                 470                 475                 480

Gly Cys Ser Pro Ser Leu Ser Gly Ala Phe Arg Val Asn Pro Trp Ser
            485                 490                 495

Val Asp Asp Val Ala Asp Ala Leu His His Ala Thr Asp Leu Thr Glu
            500                 505                 510

Ser Glu Lys Arg Leu Arg His Glu Lys His Tyr Arg Tyr Val Arg Ser
            515                 520                 525

His Ser Val Ala Tyr Trp Ala His Ser Phe Ala Gln Asp Leu Glu Arg
            530                 535                 540

Ala Cys Lys Asp His Tyr Ser Arg Arg Cys Trp Ala Ile Gly Phe Gly
545                 550                 555                 560

Leu Asn Phe Arg Val Ile Ala Leu Ser Pro Gly Phe Arg Lys Leu Ser
            565                 570                 575

Leu Glu His Phe Ala Ser Ser Tyr Asn Lys Ala Thr Arg Arg Ala Ile
            580                 585                 590

Phe Leu Asp Tyr Asp Gly Thr Leu Val Pro Gln Ser Ser Ile Asn Lys
595                 600                 605
```

```
Ala Pro Ser Asp Glu Leu Ile Thr Ile Leu Asn Ser Leu Cys Asp Asp
    610                 615                 620

Pro Lys Asn Asp Val Phe Ile Val Ser Gly Arg Ala Arg Ser Leu Leu
625                 630                 635                 640

Asp Glu Trp Phe Ala Pro Cys Gln Lys Leu Gly Ile Ala Ala Glu His
                645                 650                 655

Gly Tyr Phe Val Arg Trp Asn Lys Ala Ala Glu Trp Glu Ser Ser Tyr
            660                 665                 670

Pro Asn His Asp Phe Glu Trp Lys His Ile Ala Glu Pro Val Met Gln
        675                 680                 685

Val Tyr Thr Glu Thr Thr Asp Gly Ser Ser Ile Glu Pro Lys Glu Ser
    690                 695                 700

Ala Leu Val Trp His Tyr Leu Asp Ala Asp His Asp Phe Gly Ser Cys
705                 710                 715                 720

Gln Ala Lys Glu Leu Leu Gly His Leu Glu Arg Val Leu Ser Asn Glu
                725                 730                 735

Pro Val Val Lys Cys Gly His Tyr Ile Val Glu Val Lys Pro Gln
            740                 745                 750

Gly Val Ser Lys Gly Leu Val Val Asp Lys Val Ile His Arg Leu Met
        755                 760                 765

Asn Asn Gly Lys Thr Pro Asp Phe Val Val Cys Ile Gly Asn Asp Arg
770                 775                 780

Ser Asp Glu Asp Met Phe Lys Ser Ile Asp Ser Met Thr Ser Ser Ser
785                 790                 795                 800

Ala Phe Pro Ala Val Pro Glu Val Phe Ala Cys Ser Val Gly Gln Lys
                805                 810                 815

Pro Ser Lys Ala Lys Tyr Tyr Val Asp Asp Ala Gly Glu Val Val Arg
            820                 825                 830

Leu Leu Lys Asn Val Ala Gly Ile Ser Ser His Arg Glu Ala Val Ser
        835                 840                 845

His Gly Arg Val Thr Phe Arg Asp Val Met Asp Tyr Val Glu
    850                 855                 860

<210> SEQ ID NO 9
<211> LENGTH: 862
<212> TYPE: PRT
<213> ORGANISM: Populus balsamifera subsp. trichocarpa

<400> SEQUENCE: 9

Met Val Ser Arg Ser Tyr Ser Asn Leu Leu Asp Leu Ala Ser Gly Asp
1               5                   10                  15

Ala Pro Ile Pro Ser Phe Gly Arg Glu Arg Lys Arg Phe Pro Arg Val
            20                  25                  30

Ala Thr Val Ala Gly Ile Leu Thr Asp Leu Asp Asp Glu Asn Asn Val
        35                  40                  45

Gly Ser Asp Ser Pro Ser Ser Val Ser Leu Gly Arg Met Ile Ile Val
    50                  55                  60

Gly Asn Gln Leu Pro Leu Arg Ala His Arg Ser Pro Asp Ser Ser Gly
65                  70                  75                  80

Gly Trp Cys Phe Ser Trp Asp Glu Asp Ser Leu Leu Leu Gln Leu Lys
                85                  90                  95

Asp Gly Leu Gly Glu Gly Val Glu Val Ile Tyr Val Gly Ser Leu Lys
            100                 105                 110

Glu Glu Ile Glu Pro Ser Glu Gln Asp Asp Val Ala Gln Thr Leu Leu
        115                 120                 125
```

```
Glu Thr Phe Lys Cys Val Pro Ala Phe Ile Pro Pro Asp Leu Phe Thr
    130                 135                 140
Lys Phe Tyr His Gly Phe Cys Lys Gln His Leu Trp Pro Leu Phe His
145                 150                 155                 160
Tyr Met Leu Pro Leu Ser Pro Asp Leu Gly Gly Arg Phe Asp Arg Ser
                165                 170                 175
Leu Trp Gln Ala Tyr Val Ser Val Asn Lys Ile Phe Ala Asp Lys Val
            180                 185                 190
Lys Glu Val Ile Ser Pro Glu Asp Tyr Val Trp Val His Asp Tyr
        195                 200                 205
His Leu Met Val Leu Pro Thr Phe Leu Arg Lys Ile Phe Asn Arg Val
    210                 215                 220
Lys Leu Gly Phe Phe Leu His Ser Pro Phe Pro Ser Ser Glu Ile Tyr
225                 230                 235                 240
Arg Thr Leu Pro Val Arg Asp Glu Leu Leu Arg Ala Leu Leu Asn Ser
                245                 250                 255
Asp Leu Ile Gly Phe His Thr Phe Asp Tyr Ala Arg His Phe Leu Ser
            260                 265                 270
Cys Cys Ser Arg Met Leu Gly Leu Ser Tyr Gln Ser Lys Arg Gly Tyr
        275                 280                 285
Ile Gly Leu Glu Tyr Phe Gly Arg Thr Val Ser Ile Lys Ile Leu Pro
    290                 295                 300
Val Gly Ile His Ile Gly Gln Leu Gln Ser Val Leu Asn Leu Pro Glu
305                 310                 315                 320
Thr Glu Ser Lys Val Ala Glu Leu His Asp Gln Phe Arg Gly Gln Ala
                325                 330                 335
Val Met Leu Gly Val Asp Asp Met Asp Ile Phe Lys Gly Ile Ser Leu
            340                 345                 350
Lys Leu Leu Ala Met Glu Glu Leu Leu Thr Gln His Pro Asn Lys Arg
        355                 360                 365
Gly Glu Val Val Leu Val Gln Ile Ala Asn Pro Ala Arg Gly Arg Gly
    370                 375                 380
Arg Glu Val Gln Glu Val Gln Ser Glu Thr Lys Ala Ala Val Arg Arg
385                 390                 395                 400
Ile Asn Glu Ala Phe Gly Ser Pro Gly Tyr Thr Pro Val Val Leu Ile
                405                 410                 415
Asp Arg Pro Leu Gln Phe Tyr Glu Arg Ile Ala Tyr Tyr Ala Ile Ala
            420                 425                 430
Glu Cys Cys Leu Val Thr Ala Val Arg Asp Gly Met Asn Leu Ile Pro
        435                 440                 445
Tyr Glu Tyr Ile Ile Cys Arg Gln Gly Asn Glu Lys Leu Asp Glu Thr
    450                 455                 460
Leu Gly Arg Asp Pro Ser Ala Pro Arg Lys Ser Met Leu Val Leu Ser
465                 470                 475                 480
Glu Phe Ile Gly Cys Ser Pro Ser Leu Ser Gly Ala Ile Arg Val Asn
                485                 490                 495
Pro Trp Asn Ile Asp Ala Val Ala Glu Ala Met Asn Ser Ala Leu Val
            500                 505                 510
Val Pro Glu Pro Glu Lys Gln Met Arg His Glu Lys His His Arg Tyr
        515                 520                 525
Val Ser Thr His Asp Val Ala Tyr Trp Ala Arg Ser Phe Leu Gln Asp
    530                 535                 540
Leu Glu Arg Ala Cys Arg Asp His Val Lys Arg Arg Cys Trp Gly Phe
```

```
                                -continued 545                 550                 555                 560

Gly Phe Gly Leu Gly Phe Arg Val Ile Ala Leu Asp Pro Asn Phe Arg
                565                 570                 575

Lys Ile Ser Val Glu His Ile Val Ser Ala Tyr Lys Arg Thr Lys Asn
            580                 585                 590

Arg Val Ile Leu Leu Asp Tyr Asp Gly Thr Met Thr Leu Pro Ser Ser
        595                 600                 605

Thr Arg Thr Pro Asn Met Glu Thr Val Gly Val Leu Asn Ser Leu Cys
    610                 615                 620

Thr Asp Pro Lys Asn Val Val Phe Leu Val Ser Gly Arg Asp Arg Glu
625                 630                 635                 640

Thr Leu Thr Glu Trp Phe Ser Ser Cys Glu Lys Leu Gly Ile Ala Ala
                645                 650                 655

Glu His Gly Tyr Phe Val Arg Thr Asn His Asp Ala Glu Trp Glu Thr
            660                 665                 670

Cys Val Ser Val Pro Asp Phe Asp Trp Lys Arg Ile Ala Glu Pro Val
        675                 680                 685

Met Lys Leu Tyr Thr Glu Thr Thr Asp Gly Ser Ala Ile Glu Thr Lys
    690                 695                 700

Glu Ser Ser Leu Ala Trp Asn Tyr Gln Tyr Ala Asp Pro Asp Phe Gly
705                 710                 715                 720

Ser Cys Gln Ala Lys Glu Leu Leu Asp His Leu Glu Ser Val Leu Val
                725                 730                 735

Asn Glu Pro Val Thr Val Lys Ser Gly Gln His Thr Val Glu Val Lys
            740                 745                 750

Pro Gln Gly Val Arg Lys Gly Leu Val Ala Glu Arg Leu Leu Asp Thr
        755                 760                 765

Met Lys Leu Lys Gly Lys Leu Pro Asp Phe Val Leu Cys Val Gly Asp
    770                 775                 780

Asp Gln Ser Asp Glu Asp Met Phe Glu Val Ile Leu Ser Ala Arg Ser
785                 790                 795                 800

Gly Pro Ser Leu Ser Pro Val Ala Glu Val Phe Ala Cys Thr Val Gly
                805                 810                 815

Arg Lys Pro Ser Lys Ala Lys Tyr Tyr Leu Glu Asp Thr Ser Glu Ile
            820                 825                 830

Leu Arg Met Leu Gln Gly Leu Ala Ser Ala Leu Glu Gln Asp Ala Arg
        835                 840                 845

Ser Ala Pro Gln Ser Ser Gln Gln Val Ile Ile Asp Arg Glu
    850                 855                 860

<210> SEQ ID NO 10
<211> LENGTH: 854
<212> TYPE: PRT
<213> ORGANISM: Populus balsamifera subsp. trichocarpa

<400> SEQUENCE: 10

Met Val Ser Arg Ser Tyr Ser Asn Leu Leu Glu Leu Ala Ser Gly Glu
1               5                   10                  15

Ser Pro Ser Phe Gly Arg Met Ser Arg Ile Pro Arg Ile Met Thr
            20                  25                  30

Val Ala Gly Ile Met Ser Asp Ile Asp Asp Pro Ser Glu Ser Val
        35                  40                  45

Cys Ser Asp Pro Ser Ser Ser Thr Pro Lys Asp Arg Ile Ile Ile
    50                  55                  60

Val Ala Asn Gln Leu Pro Ile Arg Ala Gln Arg Lys Ser Asp Gly Ser
```

```
              65                  70                  75                  80
Lys Ser Trp Ile Phe Ser Trp Asp Glu Asn Ser Leu Leu Leu Gln Leu
                    85                  90                  95

Lys Asp Gly Leu Gly Asp Glu Ile Glu Val Ile Tyr Val Gly Cys
                100                 105                 110

Leu Lys Glu Glu Val His Pro Asn Glu Gln Asp Glu Val Ser Gln Ile
                115                 120                 125

Leu Leu Glu Thr Phe Lys Cys Val Pro Thr Phe Leu Pro Pro Asp Leu
    130                 135                 140

Phe Ser Arg Tyr Tyr His Gly Phe Cys Lys Gln Gln Leu Trp Pro Leu
145                 150                 155                 160

Phe His Tyr Met Leu Pro Leu Ser Pro Asp Leu Gly Gly Arg Phe Asn
                165                 170                 175

Arg Ser Leu Trp Gln Ala Tyr Val Ser Val Asn Lys Ile Phe Ala Asp
                180                 185                 190

Arg Ile Met Glu Val Ile Asn Pro Glu Asp Asp Phe Val Trp Val His
                195                 200                 205

Asp Tyr His Leu Met Ala Leu Pro Thr Phe Leu Arg Lys Arg Phe Asn
    210                 215                 220

Lys Val Lys Leu Gly Phe Phe Leu His Ser Pro Phe Pro Ser Ser Glu
225                 230                 235                 240

Ile Tyr Lys Thr Leu Pro Ile Arg Glu Glu Leu Leu Arg Ala Leu Leu
                245                 250                 255

Asn Ser Asp Leu Ile Gly Phe His Thr Phe Asp Tyr Ala Arg His Phe
                260                 265                 270

Leu Ser Cys Cys Ser Arg Met Leu Gly Leu Ser Tyr Glu Ser Lys Arg
    275                 280                 285

Gly Tyr Ile Gly Ile Glu Tyr Cys Gly Arg Thr Val Ser Ile Lys Ile
    290                 295                 300

Leu Pro Val Gly Ile His Met Gly Gln Leu Gln Ser Val Leu Ser Leu
305                 310                 315                 320

Pro Glu Thr Glu Ala Lys Val Lys Glu Leu Ile Lys Gln Phe Ser Asp
                325                 330                 335

Gln Asp Arg Ile Met Leu Leu Gly Val Asp Asp Met Asp Ile Phe Lys
                340                 345                 350

Gly Ile Ser Leu Lys Leu Leu Ala Met Glu Gln Leu Leu Met Gln His
    355                 360                 365

Pro Glu Trp Gln Gly Lys Ile Val Leu Val Gln Ile Ala Asn Pro Ala
    370                 375                 380

Arg Gly Lys Gly Lys Asp Val Lys Glu Val Gln Ala Glu Thr His Ala
385                 390                 395                 400

Ala Val Lys Arg Ile Asn Glu Thr Phe Gly Lys Pro Gly Tyr Asp Pro
                405                 410                 415

Ile Val Leu Ile Asp Ala Pro Leu Lys Phe Tyr Glu Lys Val Ala Tyr
                420                 425                 430

Tyr Val Val Ala Glu Cys Cys Leu Val Thr Ala Val Arg Asp Gly Met
                435                 440                 445

Asn Leu Ile Pro Tyr Glu Tyr Ile Ile Ser Arg Gln Gly Asn Asp Arg
    450                 455                 460

Leu Asn Lys Leu Leu Gly Gln Glu Pro Ser Thr Pro Lys Lys Ser Met
465                 470                 475                 480

Leu Val Ile Ser Glu Phe Ile Gly Cys Ser Pro Ser Leu Ser Gly Ala
                485                 490                 495
```

```
Ile Arg Val Asn Pro Trp Asn Ile Asp Ala Val Ala Asp Ala Met Asp
            500                 505                 510

Phe Ala Leu Glu Met Ala Glu Pro Glu Lys Gln Leu Arg His Glu Lys
            515                 520                 525

His Tyr Arg Tyr Val Ser Thr His Asp Val Gly Tyr Trp Ala Arg Ser
            530                 535                 540

Phe Leu Gln Asp Leu Glu Arg Thr Cys Arg Asp His Ser Arg Arg Arg
545                 550                 555                 560

Cys Trp Gly Ile Gly Phe Gly Leu Ser Phe Arg Val Val Ala Leu Asp
                565                 570                 575

Pro Asn Phe Lys Lys Leu Ser Met Glu Arg Ile Val Ser Ala Tyr Lys
            580                 585                 590

Arg Thr Thr Thr Arg Ala Ile Leu Leu Asp Tyr Asp Gly Thr Leu Met
            595                 600                 605

Pro Gln Ala Ser Ile Asp Lys Ser Pro Ser Ser Lys Ser Ile Asp Ile
            610                 615                 620

Ile Asn Asn Leu Cys Arg Asp Lys Asn Asn Met Val Phe Leu Val Ser
625                 630                 635                 640

Ala Arg Ser Arg Asn Thr Val Ala Glu Trp Phe Ser Glu Cys Glu Lys
                645                 650                 655

Leu Gly Leu Ala Ala Glu His Gly Tyr Phe Leu Arg Leu Lys Arg Asp
            660                 665                 670

Ala Glu Trp Glu Thr Arg Val Pro Val Ala Asp Thr Thr Trp Lys Gln
            675                 680                 685

Ile Ala Glu Pro Val Met Gln Leu Tyr Thr Glu Thr Asp Gly Ser
            690                 695                 700

Thr Ile Glu Asp Lys Glu Thr Ser Leu Val Trp Cys Tyr Glu Asp Ala
705                 710                 715                 720

Asp Pro Asp Phe Gly Ser Cys Gln Ala Lys Glu Leu Leu Asp His Leu
                725                 730                 735

Glu Ser Val Leu Ala Asn Glu Pro Val Thr Val Lys Ser Gly Gln Asn
            740                 745                 750

Ile Val Glu Val Lys Pro Gln Gly Val Ser Lys Gly Leu Val Ala Lys
            755                 760                 765

Arg Leu Leu Ser Ile Met Gln Glu Asn Glu Met Ser Pro Asp Phe Val
770                 775                 780

Leu Cys Ile Gly Asp Asp Arg Ser Asp Glu Asp Met Phe Glu Val Ile
785                 790                 795                 800

Thr Thr Ser Met Ala Gly Pro Ser Ile Ala Glu Asn Ala Glu Val Phe
                805                 810                 815

Ala Cys Thr Val Gly Arg Lys Pro Ser Lys Ala Lys Tyr Tyr Leu Asp
            820                 825                 830

Asp Thr Ala Glu Ile Val Arg Leu Met Gln Gly Leu Ala Ser Val Ser
            835                 840                 845

Glu Gln Thr Val Thr Val
            850

<210> SEQ ID NO 11
<211> LENGTH: 853
<212> TYPE: PRT
<213> ORGANISM: Populus balsamifera subsp. trichocarpa

<400> SEQUENCE: 11

Met Met Ser Arg Ser Tyr Thr Asn Leu Leu Asp Leu Ala Ser Gly Asn
1               5                   10                  15
```

-continued

```
Phe Pro Ala Met Gly Gln Pro Arg Glu Arg Lys Arg Leu Pro Arg Val
            20                  25                  30

Met Thr Val Pro Gly Val Ile Ser Glu Leu Asp Asp Val Ala Asn
        35                  40                  45

Ser Val Thr Ser Asp Val Pro Ser Ser Val Val Gln Asp Arg Ile Ile
    50                  55                  60

Ile Val Gly Asn Gln Leu Pro Val Lys Ala Lys Arg Arg Pro Asp Asn
65                  70                  75                  80

Lys Gly Trp Ser Phe Ser Trp Asp Glu Asp Ser Leu Leu Leu Gln Leu
                85                  90                  95

Lys Asp Gly Leu Pro Glu Glu Met Glu Val Leu Tyr Val Gly Ser Leu
            100                 105                 110

Arg Ala Asp Ile Asp Leu Ser Glu Gln Glu Asp Val Ser Gln Ile Leu
        115                 120                 125

Leu Asp Arg Phe Lys Cys Val Pro Ala Phe Leu Pro Pro Asp Ile Leu
    130                 135                 140

Ser Lys Phe Tyr His Gly Phe Cys Lys Gln Tyr Leu Trp Pro Leu Phe
145                 150                 155                 160

His Tyr Met Leu Pro Ile Ser Gly Asn His Gly Gly Arg Phe Asp Arg
                165                 170                 175

Ser Leu Trp Glu Ala Tyr Val Ala Ala Asn Lys Ile Phe Ser Gln Arg
            180                 185                 190

Val Ile Glu Val Ile Asn Pro Glu Asp Asp Tyr Val Trp Ile His Asp
        195                 200                 205

Tyr His Leu Met Val Leu Pro Thr Phe Leu Arg Arg Arg Phe Asn Arg
    210                 215                 220

Leu Arg Met Gly Phe Phe Leu His Ser Pro Phe Pro Ser Ser Glu Ile
225                 230                 235                 240

Tyr Arg Thr Leu Pro Val Arg Glu Glu Ile Leu Lys Ala Leu Leu Asn
                245                 250                 255

Ser Asp Leu Ile Gly Phe His Thr Phe Asp Tyr Ala Arg His Phe Leu
            260                 265                 270

Ser Cys Cys Ser Arg Met Leu Gly Leu Glu Tyr Gln Ser Lys Arg Gly
        275                 280                 285

Tyr Ile Gly Leu Glu Tyr Tyr Gly Arg Thr Val Gly Ile Lys Ile Met
    290                 295                 300

Pro Val Gly Ile His Met Gly Gln Ile Gln Ser Val Leu Lys Leu Ala
305                 310                 315                 320

Asp Lys Asp Trp Arg Val Glu Glu Leu Lys Gln Gln Phe Glu Gly Lys
                325                 330                 335

Thr Val Leu Leu Gly Val Asp Asp Met Asp Ile Phe Lys Gly Val Asn
            340                 345                 350

Leu Lys Leu Leu Ala Met Glu Gln Leu Leu Lys Gln His Pro Lys Trp
        355                 360                 365

Gln Arg Arg Ala Val Leu Val Gln Ile Thr Asn Pro Ala Arg Gly Arg
    370                 375                 380

Gly Arg Asp Leu Glu Glu Val Gln Ala Glu Ile Gln Glu Ser Cys Arg
385                 390                 395                 400

Arg Ile Asn Glu Thr Phe Gly Arg Pro Gly Tyr Glu Pro Val Val Phe
                405                 410                 415

Ile Asp Arg Pro Val Ser Leu Ser Glu Arg Ser Ala Tyr Phe Thr Ile
            420                 425                 430

Ala Glu Cys Val Val Ala Ala Val Arg Asp Gly Met Asn Leu Thr
        435                 440                 445
```

```
Pro Tyr Glu Tyr Ile Val Cys Arg Gln Gly Val Ser Gly Ser Glu Ser
    450                 455                 460

Ser Ser Gly Ser Ser Gly Pro Lys Lys Ser Met Leu Val Val Ser Glu
465                 470                 475                 480

Phe Ile Gly Cys Ser Pro Ser Leu Ser Gly Ala Ile Arg Val Asn Pro
                485                 490                 495

Trp Asn Ile Glu Ala Thr Ala Glu Ala Met Asn Glu Ala Ile Ser Met
            500                 505                 510

Ala Asp Ser Glu Lys Gln Leu Arg His Glu Lys His Tyr Arg Tyr Val
        515                 520                 525

Ser Thr His Asp Val Ala Tyr Trp Ser Arg Ser Phe Tyr Gln Asp Met
    530                 535                 540

Glu Arg Thr Cys Lys Asp His Phe Arg Arg Cys Trp Gly Ile Gly
545                 550                 555                 560

Leu Ser Phe Gly Phe Arg Val Val Ala Leu Asp Pro Asn Phe Lys Lys
                565                 570                 575

Leu Asn Ile Asp Gln Ile Glu Ser Ala Tyr Ile Lys Ser Lys Asn Arg
            580                 585                 590

Ala Ile Leu Leu Asp Tyr Asp Gly Thr Val Met Pro Gln Thr Thr Ile
        595                 600                 605

Asn Lys Thr Pro Asn Gln Glu Val Ile Ser Ile Asn Thr Leu Cys
610                 615                 620

Ser Asp Val Lys Asn Thr Val Phe Val Val Ser Gly Arg Gly Arg Asp
625                 630                 635                 640

Ser Leu Gly Lys Trp Phe Ala His Cys Lys Lys Leu Gly Ile Ala Ala
                645                 650                 655

Glu His Gly Tyr Phe Met Arg Trp Ser Val Asp Glu Trp Glu Asn
            660                 665                 670

Cys Gly Gln Ser Ser Asp Phe Gly Trp Thr Gln Ile Ala Glu Pro Val
        675                 680                 685

Met Asn Leu Tyr Thr Glu Ala Thr Asp Gly Ser Ser Ile Glu Thr Lys
    690                 695                 700

Glu Ser Ala Leu Val Trp His His Arg Asp Ala Asp Pro Gly Phe Gly
705                 710                 715                 720

Ala Ala Gln Ala Lys Glu Leu Leu Asp His Leu Glu Ser Val Leu Ala
                725                 730                 735

Asn Glu Pro Val Ala Val Lys Ser Gly Gln Cys Ile Val Glu Val Lys
            740                 745                 750

Pro Gln Gly Ile Ser Lys Gly Ser Val Ala Glu Lys Ile Phe Thr Ser
        755                 760                 765

Met Ala Glu Ser Gly Arg Gln Ala Asp Phe Val Leu Cys Ile Gly Asp
    770                 775                 780

Asp Arg Ser Asp Glu Asp Met Phe Glu Ser Ile Asp Asn Ala Ile Ala
785                 790                 795                 800

Asn Gly Ile Leu Thr Ser Ser Lys Ser Val Phe Ala Cys Thr Val Gly
                805                 810                 815

Gln Lys Pro Ser Lys Ala Lys Tyr Tyr Leu Asp Asp Thr Thr Asp Val
            820                 825                 830

Ile Asn Met Leu Glu Ala Leu Ala Glu Ala Ser Asp Pro Ser Pro Ser
        835                 840                 845

Ala Gly Ser Ser Pro
850
```

```
<210> SEQ ID NO 12
<211> LENGTH: 857
<212> TYPE: PRT
<213> ORGANISM: Populus balsamifera subsp. trichocarpa

<400> SEQUENCE: 12
```

| | | | | | | | | | | | | | | | |
|---|---|---|---|---|---|---|---|---|---|---|---|---|---|---|---|
| Met | Val | Ser | Ser | Ser | Cys | Ile | Ser | Leu | Leu | Asp | Leu | Ala | Ser | Gly | Asn |
| 1 | | | | 5 | | | | | 10 | | | | | 15 | |

| | | | | | | | | | | | | | | | |
|---|---|---|---|---|---|---|---|---|---|---|---|---|---|---|---|
| Met | Met | Asn | Phe | Ser | Gln | Ala | Pro | Arg | Ala | Leu | Pro | Arg | Ile | Met | Thr |
| | | | 20 | | | | | 25 | | | | | 30 | | |

| | | | | | | | | | | | | | | | |
|---|---|---|---|---|---|---|---|---|---|---|---|---|---|---|---|
| Val | Pro | Gly | Ile | Ile | Ser | Asp | Ile | Asp | Gly | Asp | Gly | Thr | Asn | Asp | Gly |
| | | | | 35 | | | | | 40 | | | | | 45 | |

| | | | | | | | | | | | | | | | |
|---|---|---|---|---|---|---|---|---|---|---|---|---|---|---|---|
| Asn | Ser | Asp | Ala | Pro | Ser | Thr | Val | Lys | Lys | Ile | Ile | Val | Ser | Asn | Phe |
| | 50 | | | | | 55 | | | | | 60 | | | | |

| | | | | | | | | | | | | | | | |
|---|---|---|---|---|---|---|---|---|---|---|---|---|---|---|---|
| Leu | Pro | Leu | Asn | Ala | Gln | Lys | Asp | Leu | Lys | Ser | Gly | Lys | Trp | Ser | Phe |
| 65 | | | | | 70 | | | | | 75 | | | | | 80 |

| | | | | | | | | | | | | | | | |
|---|---|---|---|---|---|---|---|---|---|---|---|---|---|---|---|
| Ser | Phe | Asp | Glu | Asp | Ser | Leu | Leu | Leu | Gln | Met | Lys | Asp | Gly | Phe | Ser |
| | | | | 85 | | | | | 90 | | | | | 95 | |

| | | | | | | | | | | | | | | | |
|---|---|---|---|---|---|---|---|---|---|---|---|---|---|---|---|
| Glu | Asn | Thr | Glu | Val | Val | Tyr | Val | Gly | Ser | Leu | Arg | Val | Asp | Val | Asp |
| | | | 100 | | | | | 105 | | | | | 110 | | |

| | | | | | | | | | | | | | | | |
|---|---|---|---|---|---|---|---|---|---|---|---|---|---|---|---|
| Thr | Ser | Glu | Gln | Glu | Glu | Val | Ser | Gln | Gln | Leu | Leu | Glu | Glu | Phe | Asn |
| | | | 115 | | | | | 120 | | | | | 125 | | |

| | | | | | | | | | | | | | | | |
|---|---|---|---|---|---|---|---|---|---|---|---|---|---|---|---|
| Cys | Val | Pro | Thr | Phe | Ile | Pro | Ser | Glu | Ile | Tyr | Lys | Asn | Phe | Tyr | His |
| 130 | | | | | 135 | | | | | 140 | | | | | |

| | | | | | | | | | | | | | | | |
|---|---|---|---|---|---|---|---|---|---|---|---|---|---|---|---|
| Gly | Phe | Cys | Lys | His | His | Leu | Trp | Pro | Leu | Phe | His | Tyr | Met | Leu | Pro |
| 145 | | | | | 150 | | | | | 155 | | | | | 160 |

| | | | | | | | | | | | | | | | |
|---|---|---|---|---|---|---|---|---|---|---|---|---|---|---|---|
| Met | Cys | Pro | Asp | His | Gly | Asn | Arg | Phe | Asp | Arg | Leu | Leu | Trp | Gln | Ser |
| | | | | 165 | | | | | 170 | | | | | 175 | |

| | | | | | | | | | | | | | | | |
|---|---|---|---|---|---|---|---|---|---|---|---|---|---|---|---|
| Tyr | Val | Ser | Thr | Asn | Lys | Ile | Phe | Ala | Asp | Lys | Val | Met | Gly | Val | Ile |
| | | | 180 | | | | | 185 | | | | | 190 | | |

| | | | | | | | | | | | | | | | |
|---|---|---|---|---|---|---|---|---|---|---|---|---|---|---|---|
| Asn | Ser | Glu | Glu | Asp | Tyr | Val | Trp | Val | His | Asp | Tyr | His | Leu | Met | Val |
| | | | 195 | | | | | 200 | | | | | 205 | | |

| | | | | | | | | | | | | | | | |
|---|---|---|---|---|---|---|---|---|---|---|---|---|---|---|---|
| Leu | Pro | Thr | Phe | Leu | Arg | Lys | Arg | Phe | Asn | Arg | Ile | Lys | Leu | Gly | Phe |
| | | | 210 | | | | | 215 | | | | | 220 | | |

| | | | | | | | | | | | | | | | |
|---|---|---|---|---|---|---|---|---|---|---|---|---|---|---|---|
| Phe | Leu | His | Ser | Pro | Phe | Pro | Ser | Ser | Glu | Ile | Tyr | Arg | Thr | Leu | Pro |
| 225 | | | | | 230 | | | | | 235 | | | | | 240 |

| | | | | | | | | | | | | | | | |
|---|---|---|---|---|---|---|---|---|---|---|---|---|---|---|---|
| Val | Arg | Asp | Glu | Ile | Leu | Lys | Ala | Leu | Leu | Asn | Ala | Asp | Leu | Ile | Gly |
| | | | | 245 | | | | | 250 | | | | | 255 | |

| | | | | | | | | | | | | | | | |
|---|---|---|---|---|---|---|---|---|---|---|---|---|---|---|---|
| Phe | His | Thr | Phe | Asp | Tyr | Ala | Arg | His | Phe | Leu | Ser | Cys | Cys | Ser | Arg |
| | | | 260 | | | | | 265 | | | | | 270 | | |

| | | | | | | | | | | | | | | | |
|---|---|---|---|---|---|---|---|---|---|---|---|---|---|---|---|
| Met | Leu | Gly | Leu | Tyr | Tyr | Glu | Ser | Lys | Arg | Gly | His | Ile | Gly | Leu | Glu |
| | | | 275 | | | | | 280 | | | | | 285 | | |

| | | | | | | | | | | | | | | | |
|---|---|---|---|---|---|---|---|---|---|---|---|---|---|---|---|
| Tyr | Phe | Gly | Arg | Thr | Val | Tyr | Ile | Lys | Ile | Leu | Pro | Val | Gly | Ile | His |
| | | | 290 | | | | | 295 | | | | | 300 | | |

| | | | | | | | | | | | | | | | |
|---|---|---|---|---|---|---|---|---|---|---|---|---|---|---|---|
| Met | Gly | Arg | Val | Glu | Ser | Ala | Leu | Asn | His | Pro | Ser | Ser | Ser | Ile | Lys |
| 305 | | | | | 310 | | | | | 315 | | | | | 320 |

| | | | | | | | | | | | | | | | |
|---|---|---|---|---|---|---|---|---|---|---|---|---|---|---|---|
| Val | Lys | Glu | Ile | Gln | Lys | Gln | Phe | Lys | Gly | Lys | Arg | Leu | Val | Val | Gly |
| | | | | 325 | | | | | 330 | | | | | 335 | |

| | | | | | | | | | | | | | | | |
|---|---|---|---|---|---|---|---|---|---|---|---|---|---|---|---|
| Val | Asp | Asp | Met | Asp | Ile | Phe | Lys | Gly | Ile | Ser | Leu | Lys | Leu | Leu | Ala |
| | | | 340 | | | | | 345 | | | | | 350 | | |

| | | | | | | | | | | | | | | | |
|---|---|---|---|---|---|---|---|---|---|---|---|---|---|---|---|
| Met | Glu | His | Leu | Leu | Gln | Gln | Asn | Ser | Gly | Met | Arg | Gly | Lys | Leu | Val |
| | | | 355 | | | | | 360 | | | | | 365 | | |

| | | | | | | | | | | | | | | | |
|---|---|---|---|---|---|---|---|---|---|---|---|---|---|---|---|
| Leu | Val | Gln | Ile | Val | Asn | Pro | Ala | Arg | Ser | Ser | Gly | Lys | Ala | Val | Gln |
| | | | 370 | | | | | 375 | | | | | 380 | | |

| | | | | | | | | | | | | | | | |
|---|---|---|---|---|---|---|---|---|---|---|---|---|---|---|---|
| Glu | Ala | Lys | Met | Glu | Thr | His | Thr | Ile | Thr | Lys | Arg | Ile | Asn | Asp | Thr |

```
385                 390                 395                 400

Phe Gly Phe Pro Gly Tyr Glu Pro Val Val Leu Ile Asp Arg His Val
                405                 410                 415

Pro Phe Cys Glu Lys Thr Ala Tyr Phe Ala Leu Ala Glu Cys Cys Ile
            420                 425                 430

Val Asn Ala Val Arg Asp Gly Met Asn Leu Ile Pro Tyr Lys Tyr Ile
                435                 440                 445

Ala Cys Arg Gln Gly Thr Pro Lys Met Asp Glu Ala Leu Gly Val Ala
            450                 455                 460

Ser Gly Ser Arg His Thr Ser Ser Leu Val Val Ser Glu Phe Thr Gly
465                 470                 475                 480

Cys Ser Pro Ser Leu Ser Gly Ala Ile Arg Val Asn Pro Trp Asp Ile
                485                 490                 495

Glu Ala Val Ala Asn Ala Leu Asn Val Ala Ile Thr Met Pro Asp Leu
                500                 505                 510

Glu Lys Gln Leu Arg His Glu Lys His Tyr Arg Phe Val Ser Ser His
            515                 520                 525

Asp Val Ala Tyr Trp Ala Arg Ser Phe Met Gln Asp Leu Thr Arg Ala
        530                 535                 540

Cys Glu Asp His Tyr Ser Lys Arg Cys Trp Gly Ile Gly Phe Gly Leu
545                 550                 555                 560

Asn Phe Arg Ile Leu Ser Leu Ser Pro Ser Phe Arg Lys Leu Ser Asn
                565                 570                 575

Asp Tyr Ile Ile Ser Ala Tyr Lys Arg Thr Ser Lys Arg Ala Ile Phe
                580                 585                 590

Leu Asp Tyr Asp Gly Thr Val Val Ala Gln Thr Ser Ile Pro Lys Thr
            595                 600                 605

Pro Ser Pro Glu Val Ile Ser Val Leu Asn Asn Leu Cys Ser Asp Pro
    610                 615                 620

Arg Asn Asn Val Phe Ile Val Ser Gly Arg Gly Lys Lys Ser Leu Ser
625                 630                 635                 640

Asp Trp Phe Ala Gln Cys Glu Asn Leu Gly Ile Ala Ala Glu His Gly
                645                 650                 655

Tyr Phe Leu Arg Trp Ser Gly Met Ser Asp Trp Glu Thr Arg Ser Phe
                660                 665                 670

Ala Ala Asp Phe Asp Trp Lys Asn Ile Ala Glu Pro Val Met Lys Leu
            675                 680                 685

Tyr Thr Glu Ala Thr Asp Gly Ser Tyr Ile Glu Thr Lys Glu Ser Ala
            690                 695                 700

Leu Val Trp His His Gln Asp Ala Asp Pro Asp Phe Gly Ser Cys Gln
705                 710                 715                 720

Ala Lys Glu Leu Leu Asp His Leu Glu Asn Val Leu Ala Asn Asp Pro
                725                 730                 735

Val Val Val Lys Arg Gly Gln Asn Ile Val Glu Val Lys Pro Gln Gly
                740                 745                 750

Val Thr Lys Gly Phe Val Ala Glu Lys Val Leu Ser Ser Met Ile Ala
            755                 760                 765

Asn Gly Lys Pro Pro Asp Phe Val Leu Cys Ile Gly Asp Asp Arg Ser
    770                 775                 780

Asp Glu Asp Met Phe Glu Ser Met Ser Asn Thr Ala Tyr Gly Ser Ser
785                 790                 795                 800

Leu Pro Ser Ala Pro Ala Ile Phe Ala Cys Thr Val Gly Gln Lys Pro
                805                 810                 815
```

```
Ser Lys Ala Arg Tyr Tyr Leu Asp Asp Thr Val Asp Val Leu Ala Leu
                820                 825                 830

Leu Gln Cys Leu Ala Asp Ala Ser Asn Ser Lys Ser Ser Ser Thr Glu
            835                 840                 845

Thr Gln Val Ser Phe Asp Asn Val Val
        850                 855

<210> SEQ ID NO 13
<211> LENGTH: 865
<212> TYPE: PRT
<213> ORGANISM: Populus balsamifera subsp. trichocarpa

<400> SEQUENCE: 13

Met Val Ser Arg Ser Cys Ile Ser Leu Leu Asp Phe Ala Ser Gly Asn
1               5                   10                  15

Met Met Asn Phe Ser Gln Ser Pro Arg Ser Leu Pro Arg Ile Met Thr
            20                  25                  30

Val Pro Gly Ile Ile Ser Asp Val Asp Val Asp Gly Ile Asn Asp Gly
        35                  40                  45

Ile Ser Asp Ala Pro Ser Thr Gly Ser Gly Ala Lys Met Ile Ile Val
50                  55                  60

Ser Asn Phe Leu Pro Leu Asn Ala Gln Lys Asp Leu Asn Ser Gly Lys
65                  70                  75                  80

Trp Ser Phe Ser Phe Asp Glu Asp Ser Leu Leu Leu Gln Met Lys Asp
                85                  90                  95

Gly Phe Ser Ala Ile Pro Glu Val Val Tyr Val Gly Ser Leu Arg Val
            100                 105                 110

Asp Val Asp Ser Ser Glu Gln Glu Val Ser Gln Lys Leu Leu Glu
        115                 120                 125

Glu Phe Asn Cys Val Pro Thr Phe Ile Pro Pro Asp Ile Tyr Lys Asn
130                 135                 140

Phe Tyr His Gly Phe Cys Lys His His Leu Trp Pro Leu Phe His Tyr
145                 150                 155                 160

Met Leu Pro Leu Cys Pro Asp His Gly Asn Arg Phe Asp Arg Leu Leu
                165                 170                 175

Trp Gln Ala Tyr Val Ser Ala Asn Lys Ile Phe Ala Asp Lys Val Thr
            180                 185                 190

Glu Val Ile Asn Asn Thr Glu Asp Tyr Val Trp Val His Asp Tyr
        195                 200                 205

His Leu Met Val Leu Pro Thr Phe Leu Arg Lys Arg Phe Asn Arg Ile
210                 215                 220

Lys Leu Gly Phe Phe Leu His Ser Pro Phe Pro Ser Ser Glu Ile Tyr
225                 230                 235                 240

Arg Thr Leu Leu Val Arg Asp Glu Ile Leu Lys Ala Leu Leu Asn Ala
                245                 250                 255

Asp Leu Ile Gly Phe His Thr Phe Asp Tyr Ala Arg His Phe Leu Ser
            260                 265                 270

Cys Cys Ser Arg Met Leu Gly Leu Asp Tyr Glu Ser Lys Arg Gly His
        275                 280                 285

Ile Gly Leu Glu Tyr Phe Gly Arg Thr Val Tyr Ile Lys Ile Leu Pro
290                 295                 300

Val Gly Ile His Met Gly Arg Val Glu Ser Ala Leu Asn His Pro Ser
305                 310                 315                 320

Ser Ser Ile Lys Val Lys Glu Ile Gln Glu Gln Phe Lys Gly Lys Arg
                325                 330                 335
```

-continued

```
Leu Val Ile Gly Val Asp Asp Met Asp Ile Phe Lys Gly Ile Ser Leu
            340                 345                 350
Lys Leu Leu Ala Val Glu His Leu Leu Gln Asn Ser Glu Leu Arg
            355                 360                 365
Gly Lys Leu Val Leu Val Gln Ile Val Asn Pro Ala Arg Ser Ser Gly
            370                 375                 380
Lys Asp Val Gln Glu Ala Lys Met Glu Ile Tyr Ser Ile Thr Lys Arg
385                 390                 395                 400
Ile Asn Asn Thr Phe Gly Phe Pro Gly Tyr Glu Pro Val Val Leu Ile
            405                 410                 415
Asp Arg His Val Pro Phe Cys Glu Lys Thr Ala Tyr Tyr Ala Leu Ala
            420                 425                 430
Glu Cys Cys Ile Val Asn Ala Val Arg Asp Gly Met Asn Leu Ile Pro
            435                 440                 445
Tyr Lys Tyr Ile Val Cys Arg Gln Gly Thr Pro Lys Met Asp Glu Ala
            450                 455                 460
Leu Gly Val Ala Ser Gly Ser Arg His Thr Ser Ser Leu Val Val Ser
465                 470                 475                 480
Glu Phe Thr Gly Cys Ser Pro Ser Leu Ser Gly Ala Ile Arg Val Asn
            485                 490                 495
Pro Trp Asp Ile Glu Ala Val Ala Asn Ala Val Asn Thr Ala Ile Asn
            500                 505                 510
Met Pro Asp Leu Glu Lys Gln Leu Arg His Gly Lys His Tyr Cys Tyr
            515                 520                 525
Val Ser Ser His Asp Val Ala Tyr Trp Ala Arg Ser Phe Met Gln Asp
            530                 535                 540
Leu Lys Arg Ala Cys Lys Asp His Tyr Ser Lys Arg Cys Trp Gly Ile
545                 550                 555                 560
Gly Phe Gly Leu Asn Phe Arg Ile Leu Ala Leu Ser Pro Ser Phe Arg
            565                 570                 575
Lys Leu Ser Asn Asp Tyr Ile Ile Ser Ala Tyr Lys Arg Thr Ser Lys
            580                 585                 590
Arg Ala Ile Phe Leu Asp Tyr Asp Gly Thr Met Val Pro His Thr Ser
            595                 600                 605
Leu Ala Lys Thr Pro Thr Pro Glu Val Ile Ser Val Leu Asn Asn Leu
            610                 615                 620
Cys Ala Asp Pro Met Asn Ser Val Phe Ile Val Ser Gly Arg Gly Lys
625                 630                 635                 640
Lys Ser Leu Ser Asp Trp Phe Val Gln Cys Glu Asn Leu Gly Ile Ala
            645                 650                 655
Ala Glu His Gly Tyr Phe Phe Arg Trp Ser Gly Met Ser Asp Trp Glu
            660                 665                 670
Thr Ser Ser Leu Ala Val Asp Phe Asp Trp Lys Asn Ile Ala Glu Pro
            675                 680                 685
Val Met Lys Leu Tyr Thr Glu Ala Thr Asp Gly Ser Tyr Ile Glu Val
            690                 695                 700
Lys Glu Ser Ala Leu Val Trp His His Gln Asp Ala Asp Pro Asp Phe
705                 710                 715                 720
Gly Ser Cys Gln Ala Lys Glu Leu Leu Asp His Leu Glu Asn Val Leu
            725                 730                 735
Ala Asn Asp Pro Val Ala Val Lys Arg Gly Gln Asn Ile Val Glu Val
            740                 745                 750
Lys Pro Gln Gly Val Thr Lys Gly Phe Val Ala Glu Lys Val Leu Ser
            755                 760                 765
```

```
Lys Met Ile Ala Ser Gly Lys Pro Gly Phe Val Leu Cys Ile Gly
        770                 775                 780

Asp Asp Arg Ser Asp Glu Asp Met Phe Glu Ser Ile Ser Lys Thr Pro
785                 790                 795                 800

Tyr Ser Ser Ser Leu Pro Ser Ala Pro Ala Ile Phe Ala Cys Thr Val
            805                 810                 815

Gly Gln Lys Pro Ser Lys Ala Arg Tyr Tyr Leu Asp Asp Thr Val Asp
        820                 825                 830

Val Leu Ala Leu Leu Gln Cys Leu Ala Asp Ala Ser Ser Ser Asn Leu
        835                 840                 845

Ser Ser Thr Glu Thr Gln Val Ser Phe Asp Asn Val Val Arg Lys Glu
        850                 855                 860

Leu
865

<210> SEQ ID NO 14
<211> LENGTH: 854
<212> TYPE: PRT
<213> ORGANISM: Populus balsamifera subsp. trichocarpa

<400> SEQUENCE: 14

Met Ile Thr Gln Ser Cys Lys Asp Asn Leu Asp Met Ile Ser Val Asn
1               5                   10                  15

Asp Phe Arg Val Val Asp Arg Ile Pro Arg Ile Met Asn Val Leu Gly
                20                  25                  30

Ala Leu Ser Glu Ile Glu Val Gly Glu His Asp Glu Gly Val Thr
            35                  40                  45

Ser Pro Val Val Ser Lys Pro Arg Arg Ile Met Val Ala Asn Gln Leu
    50                  55                  60

Pro Ile Arg Gly His Arg Asn Glu Glu Thr Lys Gly Trp Ser Phe Glu
65                  70                  75                  80

Leu Asp Lys Glu Ser Leu Val Leu Gln Phe Lys Asp Gly Phe Pro Ala
                85                  90                  95

Asn Ser Glu Val Trp Tyr Val Gly Leu Leu Lys Val Asp Val Glu Thr
            100                 105                 110

Lys Asp Gln Asp Glu Val Ala Arg Leu Leu Phe Ser Met Phe Arg Cys
        115                 120                 125

Val Pro Val Phe Leu Thr Asp Asp Gln Lys Asn Lys Tyr Tyr His Gly
    130                 135                 140

Phe Cys Lys His Tyr Leu Trp Pro Leu Phe His Tyr Met Leu Pro Leu
145                 150                 155                 160

Ser Pro Ser Arg Gly Gly Val Arg Phe Asp Arg Ser Leu Trp Glu Gly
                165                 170                 175

Tyr Ile Val Ala Asn Arg Leu Phe Ala Asn Lys Val Thr Glu Ile Leu
            180                 185                 190

Arg His His Glu Asp Ser Val Trp Val His Asp Tyr His Leu Met Val
        195                 200                 205

Leu Pro Ala Phe Leu Arg Lys Arg Phe Asn Arg Val Lys Leu Gly Phe
    210                 215                 220

Phe Leu His Ser Pro Phe Pro Ser Ser Glu Ile Tyr Thr Thr Ile Pro
225                 230                 235                 240

Val Arg Glu Glu Ile Leu Arg Ser Leu Leu Asn Cys Asp Leu Ile Gly
                245                 250                 255

Phe His Thr Phe Asp Tyr Ala Arg His Phe Leu Ser Cys Cys Ser Lys
            260                 265                 270
```

```
Met Leu Gly Ile Asp Tyr Gln Cys Lys Arg Gly Tyr Ile Gly Leu Asp
        275                 280                 285
Tyr Cys Gly Lys Thr Ile Ser Ile Lys Ile Leu His Met Gly Ile His
        290                 295                 300
Met Gly Gln Leu Glu Ser Val Leu Asn Met Glu Gln Thr Ala Thr Leu
305                 310                 315                 320
Ala Lys Gln Leu Lys Glu Lys Phe Glu Gly Lys Ile Val Met Val Gly
                325                 330                 335
Val Asp Asp Leu Asp Leu Leu Lys Gly Ile Ser Ser Lys Phe Ser Ala
                340                 345                 350
Met Gly Arg Leu Leu Glu Met Arg Pro Glu Leu Ile Gly Lys Val Val
                355                 360                 365
Leu Val Gln Ile Ala Asn Pro Ala Arg Ser Gln Gly Lys Asp Val Gln
        370                 375                 380
Glu Val Gln Lys Glu Thr Thr Leu Ile Ala Gln Gln Ile Asn Gln Lys
385                 390                 395                 400
Tyr Gly Tyr Glu Gly Tyr Gln Pro Ile Val Phe Ile Asn Gly Pro Val
                405                 410                 415
Ser Thr Leu Glu Lys Ala Ala Tyr Ala Ile Ser Glu Cys Cys Val
                420                 425                 430
Val Asn Ala Leu Arg Asp Gly Met Asn Leu Val Ser Tyr Lys Tyr Thr
        435                 440                 445
Val Cys Arg Gln Gly Ser Pro Val Leu Asp Lys Ala Leu Gly Ile Asp
        450                 455                 460
Glu Ser Tyr Pro Arg Lys Ser Phe Leu Ile Val Ser Glu Phe Ile Gly
465                 470                 475                 480
Cys Ser Pro Ser Leu Ser Gly Ala Arg Arg Val Asn Pro Trp Asp Val
                485                 490                 495
Gly Ala Val Ala Asp Ala Met Tyr Ala Gly Ile His Met Lys Asp Glu
                500                 505                 510
Glu Lys His Leu Arg His Glu Lys His Tyr Lys Tyr Ile Ser Ser His
                515                 520                 525
Asp Val Ala Phe Trp Ala Arg Ser Phe Asp Leu Asp Leu Glu Arg Ala
        530                 535                 540
Cys Lys Asp His Tyr Leu Lys Arg Tyr Asn Val Gly Phe Gly Leu
545                 550                 555                 560
Asn Phe Arg Val Ala Ala Val Gly Thr Asn Phe Arg Met Leu Thr Thr
                565                 570                 575
Glu Arg Val Val Ala Ala Tyr Asn Asn Thr Asn Ser Arg Leu Ile Leu
                580                 585                 590
Leu Asp Tyr Asp Gly Thr Met Met Pro Gln Cys Ala Val Asp Lys Thr
        595                 600                 605
Pro Arg Ser Glu Val Ile Ser Ile Leu Asn Cys Leu Cys Ser Asp Pro
610                 615                 620
Lys Asn Val Val Phe Ile Val Ser Gly Arg Gly Arg Asp Pro Leu Ser
625                 630                 635                 640
Lys Trp Phe Ser Pro Cys Glu Thr Leu Gly Ile Ser Ala Glu His Gly
                645                 650                 655
Tyr Phe Thr Arg Trp Thr Lys Asn Ser Pro Trp Glu Thr Cys Ser Val
                660                 665                 670
Ala Met Asp Cys Asp Trp Lys Lys Ile Val Gln Pro Val Met Glu Arg
                675                 680                 685
Tyr Thr Glu Thr Thr Asp Gly Ser Phe Ile Glu Pro Lys Glu Ser Ala
```

```
                690             695             700
Leu Val Trp His His Gln Asp Ala Asp Pro Asp Phe Gly Ser Cys Gln
705                 710                 715                 720

Ala Lys Glu Leu Leu Asp His Leu Glu Ser Val Leu Ala Asn Glu Pro
                725                 730                 735

Val Val Val Arg Arg Gly Gln Gln Ile Val Glu Val Lys Pro Gln Gly
                740                 745                 750

Val Ser Lys Gly Ile Val Glu Asn Leu Ile Ser Thr Met Arg Ser
                755                 760                 765

Gln Gly Lys Ser Pro Asp Phe Leu Phe Cys Ile Gly Asp Arg Ser
770                 775                 780

Asp Glu Asp Met Phe Glu Ser Ile Ala Arg Leu Val Asp Asn Pro Ser
785                 790                 795                 800

Ile Pro Pro Ile Ala Glu Val Phe Ala Cys Thr Val Gly Leu Lys Pro
                805                 810                 815

Ser Lys Ala Lys Tyr Tyr Leu Asp Asp Thr Pro Glu Val Ile Lys Leu
                820                 825                 830

Leu Gln Gly Leu Ala Thr Ala Ser Val Gly Ser Lys Tyr Ala His Thr
                835                 840                 845

Leu Glu Asp Glu Asp Val
                850

<210> SEQ ID NO 15
<211> LENGTH: 846
<212> TYPE: PRT
<213> ORGANISM: Populus balsamifera subsp. trichocarpa

<400> SEQUENCE: 15

Met Ile Thr Gln Ser Cys Lys Asp Ser Leu Asp Met Ile Ser Val Asn
1               5                   10                  15

Asp Phe Arg Gly Leu Glu Arg Ile Pro Ala Val Met Asn Glu Leu Gly
            20                  25                  30

Tyr Glu Val Gly Asp Glu His Gly Gln Gly Pro Val Val Ser Lys Gln
        35                  40                  45

Arg Arg Ile Ile Val Ala Asn Gln Leu Pro Ile Arg Gly Tyr Arg Asn
    50                  55                  60

Glu Gly Thr Lys Gly Trp Phe Phe Glu Phe Asp Lys Asp Ser Leu Val
65                  70                  75                  80

Leu Gln Leu Lys Asp Gly Phe Pro Ala Asn Thr Glu Val Trp Tyr Val
                85                  90                  95

Gly Met Leu Lys Val Asp Val Glu Lys Glu Asp Gln Glu Glu Val Ala
            100                 105                 110

Gln Leu Met Phe His Lys Phe Arg Cys Val Pro Val Phe Leu Thr Val
        115                 120                 125

Asp Gln Lys Asn Lys Phe Tyr His Gly Phe Cys Lys His Tyr Leu Trp
    130                 135                 140

Pro Leu Phe His Tyr Met Leu Pro Leu Ser Pro Ser His Gly Gly Val
145                 150                 155                 160

Arg Phe Asp Lys Ser Leu Trp Glu Gly Tyr Ile Val Ala Asn Gln Leu
                165                 170                 175

Phe Ala Asn Lys Val Ala Glu Ile Leu Trp Pro Asp Lys Asp Ser Val
            180                 185                 190

Trp Val His Asp Tyr His Leu Met Val Leu Pro Ser Ile Leu Arg Asn
        195                 200                 205

Arg Tyr Thr Arg Val Lys Leu Gly Phe Phe Leu His Ser Pro Phe Pro
```

```
                210                 215                 220
Ser Ser Glu Ile Tyr Arg Thr Ile Pro Val Arg Glu Gln Ile Leu Arg
225                 230                 235                 240

Ser Leu Leu Asn Cys Asp Leu Ile Gly Phe His Thr Phe Asp Tyr Ala
            245                 250                 255

Arg His Phe Leu Ser Cys Cys Ser Arg Leu Leu Gly Ile Asp Tyr Gln
                260                 265                 270

Cys Lys Arg Gly Tyr Ile Gly Leu Asp Tyr Cys Gly Lys Thr Ile Asn
            275                 280                 285

Ile Lys Ile Leu Pro Val Gly Ile His Met Gly Gln Leu Glu Ser Asp
290                 295                 300

Leu Asn Met Glu Gln Thr Ala Thr Leu Ala Lys Gln Leu Lys Glu Lys
305                 310                 315                 320

Phe Glu Gly Lys Val Val Met Val Gly Val Asp Asp Leu Asp Met Phe
                325                 330                 335

Lys Gly Ile Ser Leu Lys Phe Ser Ala Met Gly Arg Leu Leu Glu Met
            340                 345                 350

His Pro Glu Leu Ile Gly Ser Val Val Leu Val Gln Ile Ala Asn Pro
                355                 360                 365

Ala Arg Ser Arg Gly Lys Asp Val Gln Glu Val Arg Leu Glu Thr Ser
370                 375                 380

Val Ile Ala Gln Gln Ile Asn Asn Lys Tyr Gly Lys Glu Gly Tyr Glu
385                 390                 395                 400

Pro Ile Val Phe Ile Asn Asp Pro Leu Ser Ala Leu Glu Lys Ala Ala
                405                 410                 415

Tyr Tyr Ala Ile Ser Glu Cys Cys Val Val Asn Ala Val Arg Asp Gly
            420                 425                 430

Met Asn Leu Val Ser Tyr Lys Tyr Thr Val Cys Arg Gln Gly Ser Pro
            435                 440                 445

Val Leu Asp Lys Ala Leu Gly Ile Asn Glu Ser Asp Gln Arg Lys Ser
450                 455                 460

Phe Leu Ile Val Ser Glu Phe Ile Gly Cys Ser Pro Ser Leu Ser Gly
465                 470                 475                 480

Ala Tyr Arg Val Asn Pro Trp Asp Val Asn Ala Val Ala Asp Ala Met
                485                 490                 495

Tyr Val Gly Ile His Met Lys Asp Glu Lys His Leu Arg His Glu
            500                 505                 510

Lys His Tyr Asn Tyr Ile Ser Ser His Asp Val Ala Phe Trp Ala Arg
            515                 520                 525

Ser Phe Asp Gln Asp Leu Asp Arg Ala Cys Lys Glu His His Leu Lys
530                 535                 540

Arg Tyr Tyr Asn Val Gly Phe Gly Leu Asn Phe Arg Ala Ala Ala Val
545                 550                 555                 560

Gly Lys Asn Phe Arg Met Leu Thr Val Glu Thr Val Ala Ala Tyr
                565                 570                 575

Asn Asn Thr Asn Ser Arg Leu Ile Leu Leu Asp Tyr Asp Gly Thr Met
            580                 585                 590

Lys Pro Lys Ser Ala Val Asp Lys Thr Pro Arg Asn Glu Val Ile Ser
            595                 600                 605

Ile Leu Asn Cys Leu Cys Ser Asp Pro Lys Asn Ile Val Phe Ile Val
            610                 615                 620

Ser Gly Arg Gly Arg Asp Pro Leu Ser Lys Trp Phe Ser Pro Cys Glu
625                 630                 635                 640
```

```
Lys Leu Gly Ile Ser Ala Glu His Gly Tyr Phe Thr Arg Trp Thr Arg
                645                 650                 655

Asp Ser Gln Trp Glu Thr Cys Ser Val Ala Met Asp Cys Asp Trp Lys
            660                 665                 670

Lys Thr Val Glu Pro Val Met Glu Val Tyr Thr Ala Thr Thr Asp Gly
        675                 680                 685

Ser Phe Ile Glu His Lys Glu Ser Ala Leu Val Trp His Tyr Gln Asp
    690                 695                 700

Ala Asp Pro Asp Phe Gly Gly Cys Gln Ala Lys Glu Leu Leu Asp His
705                 710                 715                 720

Leu Glu Ser Val Leu Ala Asn Glu Pro Val Val Lys Arg Gly Arg
                725                 730                 735

Gln Ile Val Glu Val Lys Pro Gln Gly Val Ser Lys Gly Val Val Val
            740                 745                 750

Glu Asp Leu Ile Ser Ser Met Arg Ser Lys Gly Lys Ser Pro Asp Phe
        755                 760                 765

Leu Phe Cys Ile Gly Asp Asp Arg Ser Asp Glu Asp Met Phe Glu Ser
    770                 775                 780

Ile Ala Arg Leu Phe Asp Asn Pro Ser Leu Pro Pro Ile Ala Glu Val
785                 790                 795                 800

Phe Ala Cys Thr Val Gly His Lys Pro Ser Lys Ala Lys Tyr Tyr Leu
                805                 810                 815

Asp Asp Thr Pro Asp Val Ile Glu Leu Leu Gln Gly Leu Ala Thr Ala
            820                 825                 830

Ser Val Gly Pro Lys Val Thr His Thr Leu Glu Glu Asp Ile
        835                 840                 845

<210> SEQ ID NO 16
<211> LENGTH: 6
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (5)..(5)
<223> OTHER INFORMATION: Xaa can be G or D

<400> SEQUENCE: 16

Leu Asp Tyr Asp Xaa Thr
1               5

<210> SEQ ID NO 17
<211> LENGTH: 6
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (4)..(4)
<223> OTHER INFORMATION: Xaa can be R or Q

<400> SEQUENCE: 17

Gly Asp Asp Xaa Ser Asp
1               5

<210> SEQ ID NO 18
<211> LENGTH: 49
<212> TYPE: DNA
<213> ORGANISM: Artificial
<220> FEATURE:
<223> OTHER INFORMATION: Forward primer
```

```
<400> SEQUENCE: 18
ggggacaagt tgtacaaaa aagcaggctc cgaagtaact tctacctcc                49

<210> SEQ ID NO 19
<211> LENGTH: 50
<212> TYPE: DNA
<213> ORGANISM: Artificial
<220> FEATURE:
<223> OTHER INFORMATION: Reverse primer

<400> SEQUENCE: 19
ggggaccact ttgtacaaga aagctgggtc ccatctctaa gttgtaactg              50

<210> SEQ ID NO 20
<211> LENGTH: 31
<212> TYPE: DNA
<213> ORGANISM: Artificial
<220> FEATURE:
<223> OTHER INFORMATION: Forward primer

<400> SEQUENCE: 20
cgggatccat ggtgtcaaga tcttgtgcta a                                  31

<210> SEQ ID NO 21
<211> LENGTH: 30
<212> TYPE: DNA
<213> ORGANISM: Artificial
<220> FEATURE:
<223> OTHER INFORMATION: Reverse primer

<400> SEQUENCE: 21
aaggcctaac gatgctttca aatgcaactt                                    30

<210> SEQ ID NO 22
<211> LENGTH: 23
<212> TYPE: DNA
<213> ORGANISM: Artificial
<220> FEATURE:
<223> OTHER INFORMATION: Forward primer AtTPS5

<400> SEQUENCE: 22
tcctgcttat atcccacctg agc                                           23

<210> SEQ ID NO 23
<211> LENGTH: 21
<212> TYPE: DNA
<213> ORGANISM: Artificial
<220> FEATURE:
<223> OTHER INFORMATION: Reverse primer AtTPS5

<400> SEQUENCE: 23
gcgccgctta aagaaggaga a                                             21

<210> SEQ ID NO 24
<211> LENGTH: 22
<212> TYPE: DNA
<213> ORGANISM: Artificial
<220> FEATURE:
<223> OTHER INFORMATION: left border T-DNA primer

<400> SEQUENCE: 24
tggttcacgt agtgggccat cg                                            22

<210> SEQ ID NO 25
<211> LENGTH: 20
```

```
<212> TYPE: DNA
<213> ORGANISM: Artificial
<220> FEATURE:
<223> OTHER INFORMATION: Forward primer Genetrap

<400> SEQUENCE: 25
ttgggcgcgt agctttatac                                              20

<210> SEQ ID NO 26
<211> LENGTH: 24
<212> TYPE: DNA
<213> ORGANISM: Artificial
<220> FEATURE:
<223> OTHER INFORMATION: Reverse primer Genetrap

<400> SEQUENCE: 26
caagaagata tgaaaacagc ctca                                         24

<210> SEQ ID NO 27
<211> LENGTH: 20
<212> TYPE: DNA
<213> ORGANISM: Artificial
<220> FEATURE:
<223> OTHER INFORMATION: DS5 primer

<400> SEQUENCE: 27
tacgataacg gtcggtacgg                                              20

<210> SEQ ID NO 28
<211> LENGTH: 20
<212> TYPE: DNA
<213> ORGANISM: Artificial
<220> FEATURE:
<223> OTHER INFORMATION: Forward primer line 6

<400> SEQUENCE: 28
ttgggcgcgt agctttatac                                              20

<210> SEQ ID NO 29
<211> LENGTH: 20
<212> TYPE: DNA
<213> ORGANISM: Artificial
<220> FEATURE:
<223> OTHER INFORMATION: Forward primer

<400> SEQUENCE: 29
gcactcctca acgctgattt                                              20

<210> SEQ ID NO 30
<211> LENGTH: 20
<212> TYPE: DNA
<213> ORGANISM: Artificial
<220> FEATURE:
<223> OTHER INFORMATION: Reverse primer

<400> SEQUENCE: 30
aagccctatg gttccacgtt                                              20
```

USE OF TREHALOSE-6-PHOSPHATE SYNTHASE TO MODULATE PLANT GROWTH

CROSS-REFERENCE TO RELATED APPLICATIONS

This is a national phase entry under 35 U.S.C. §371 of International Patent Application PCT/EP2007/00736 filed Jan. 29, 2007, and published in English as International Patent Publication WO 2007/085483 on Aug. 2, 2008, which claims priority to European Patent Application Serial Nos. EP 06100950.2 filed Jan. 27, 2006 and EP 06112770.0 filed Apr. 19, 2006, the entire contents of each of which are hereby incorporated herein by this reference.

TECHNICAL FIELD

The present invention relates to the use of a plant trehalose-6-phosphate synthase class II to modulate plant growth. More specifically, it relates to the use of a class II trehalose-6-phosphate synthase, comprising both a synthase-like and a phosphatase-like part to modulate plant growth. Preferably, the activity of the class II trehalose-6-phosphate synthase is down-regulated to obtain an increased plant biomass yield.

BACKGROUND

Trehalose is a widespread disaccharide, occurring in bacteria, fungi, insects and plants. In microbes, trehalose accumulation is generally associated with stress resistance, not at least with desiccation and osmotic stress resistance. In plants, however, except for some resurrection plants such as *Selaginella lepidophylla*, the role of trehalose is less clear.

In most cases, trehalose synthesis is a two-step process in which trehalose-6-phosphate synthase (TPS) synthesizes trehalose-6-phosphate (T6P), followed by a dephosphorylation to trehalose by T6P phosphatase (TPP). Although in most plants trehalose is hardly detectable, multiple homologues of both TPS and TPP genes are present, e.g., in *Arabidopsis* (Vogel et al., 2001; Leyman et al., 2001; Eastmond et al., 2003). Trehalose accumulation obtained in transgenic plants, transformed with heterologous trehalose biosynthesis genes, leads to an improved abiotic stress tolerance (Garg et al., 2002; Jang et al., 2003). However, the absence of significant trehalose accumulation in most plants, in spite of the presence of multiple trehalose biosynthesis genes, argues for a regulatory role of the gene products, rather than for a role of trehalose as stress protectant. Indeed, several authors suggest a regulatory role for TPS (Avonce et al., 2004) and its gene product T6P in sugar metabolism (Eastmond et al., 2003) and starch synthesis (Kolbe et al., 2005). T6P is indispensable for carbohydrate utilization and growth (Schluepmann et al., 2003), but accumulation of T6P seems to cause growth inhibition in seedlings (Schluepmann et al., 2004). The present data are sometimes conflicting and the role of the trehalose biosynthesis genes is still far from clear. None of these publications makes a link with a possible role of plant TPS, in particular class II plant TPS, in plant growth and yield.

EP0901527 discloses the regulation of plant metabolism by modifying the level of T6P. More specifically, they claim an increase in the yield of plants by increasing the intracellular availability of trehalose-6-phosphate. However, rather conflicting, they also claim the stimulation of growth of a plant cell or tissue by decreasing the intracellular availability of trehalose-6-phosphate. Again, as shown in the recent literature, this is indicating that the T6P balance is very delicate and far from straightforward. The inventors realized the modulation of the T6P content by expressing heterologous TPS and TPP genes in the plant. Although the patent mentions that similar results can be obtained by up- or down-regulation of the endogenous genes, one would expect that, due to the large number of plant genes, the deletion or over-expression of one of those genes has only a limited effect on the T6P concentration, if any effect at all. This is especially true for the class II TPS genes, where both a synthase-like domain and a phosphatase-like domain are present. If both domains are active, trehalose, rather than T6P, would be the end product. Moreover, for at least two *Arabidopsis* class II TPS genes, AtTPS7 and AtTPS8, no synthase nor phosphatase activity could be detected (Vogel et al., 2001; Eastmond et al., 2003), implying that a manipulation of these genes would not affect the T6P content of the plant at all.

Surprisingly, we found that a plant class II TPS can be used to modulate plant growth and biomass yield. Indeed, contrary to what would be expected on the basis of the literature, inactivation of plant TPS activity leads to increased stem and root growth, and increased plant biomass.

DISCLOSURE OF THE INVENTION

A first aspect of the invention is the use of a plant class II TPS for the modulation of plant growth. The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest. Plants that are particularly useful in the methods of the invention include all plants that belong to the superfamily Viridiplantae, in particular, monocotyledonous and dicotyledonous plants. As a non-limiting example, it may be a crop used for food or fodder, whereby the increase of roots, leaves, stem or seed biomass is increasing the crop yield. Alternatively, the crop may be used for ornamental or industrial purposes, such as starch production, or it may be used as raw material for biofuel production. Crops known for biofuel are known to the person skilled in the art and include, but are not limited to, food crops such as corn, soybean, flaxseed, rapeseed, sugar cane; industrial crops such as hemp and switchgrass; and woody biomass such as poplar and willow.

"TPS" as used herein refers to the structural homology of the gene and protein with other members of the trehalose-6-phosphate family, but does not imply that the protein has an effective trehalose-6-phosphate-synthesizing activity. Preferably, TPS has a domain homologous to the glycosyltransferase 20 (pfam00982.12). The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or activity of a protein. Identified by their high degree of conservation in aligned sequences of a family of protein homologues, they can be used as identifiers to determine if any polypeptide in question belongs to a previously identified polypeptide family. As a non-limiting example, due to its structure, "TPS" as used herein may have a T6P phosphatase activity or a combination of synthase and phosphatase activity. The use of TPS, as mentioned here, covers the use of the gene, the use of the protein, as well as the use of compounds increasing or decreasing the activity of the protein. As a non-limiting example, a compound decreasing the activity of the TPS may be an inactivating TPS antibody.

Preferably, the TPS is a class II TPS, according to the classification in *Arabidopsis thaliana*. A class II TPS comprises both a trehalose-6-phosphate synthase like domain, as well as a trehalose-6-phosphate phosphatase like domain (Leyman et al, 2001, Vogel et al., 2001), preferably the class II TPS comprises a trehalose-6-phosphate synthase like domain, as well as a trehalose-6-phosphate phosphatase-like domain comprising a phosphatase box with the sequence LDYD (G/D) T (SEQ ID NO:16) and/or a phosphatase box with the sequence GDD(R/Q)SD (SEQ ID NO:17), more preferably the class II TPS comprises both a trehalose-6-phosphate synthase like domain, as well as a trehalose-6-phosphate phosphatase like domain comprising at least one, preferably two phosphatase boxes as described by Leyman et al. (2001). Even more preferably, the TPS is selected from the group consisting of SEQ ID NOs: 1-15 (AtTPS5-11, rice orthologue, poplar orthologues), or homologues, orthologues or paralogues thereof. "Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. A deletion refers to removal of one or more amino acids from a protein. An insertion refers to one or more amino acid residues being introduced into a predetermined site in a protein. Insertions may comprise N-terminal and/or C-terminal fusions as well as intra-sequence insertions of single or multiple amino acids. A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide; insertions will usually be of the order of about 1 to 10 amino acid residues. The amino acid substitutions are preferably conservative amino acid substitutions. Conservative substitution tables are well known in the art.

"Orthologues" and "paralogues" encompass evolutionary concepts used to describe the ancestral relationships of genes. Paralogues are genes within the same species that have originated through duplication of an ancestral gene and orthologues are genes from different organisms that have originated through speciation. Orthologues and paralogues may easily be found by performing a so-called reciprocal blast search. Typically, this involves a first BLAST involving BLASTing SEQ ID NO:1 or SEQ ID NO:4 as query sequence, using BLASTP or TBLASTN (using standard default values). The BLAST results may optionally be filtered. The full-length sequences of either the filtered results or non-filtered results are then BLASTed back (second BLAST) against sequences from the organism from which the query sequence is derived (where the query sequence corresponds to AtTPS8 or AtTPS5, the second BLAST would, therefore, be against *Arabidopsis thaliana* sequences). The results of the first and second BLASTs are then compared. A paralogue is identified if a high-ranking hit from the first blast is from the same species as from which the query sequence is derived. A BLAST back, then, ideally results in the query sequence amongst the highest hit. An orthologue is identified if a high-ranking hit in the first BLAST is not from the same species as from which the query sequence is derived and, preferably, results upon BLAST back in the query sequence being among the highest hits. High-ranking hits are those having a low E-value. The lower the E-value, the more significant the score (or in other words, the lower the chance that the hit was found by chance). Computation of the E-value is well known in the art. In addition to E-values, comparisons are also scored by percentage identity. Percentage identity refers to the number of identical amino acids between the two compared polypeptide sequences over a particular length. In the case of large families, ClustalW may be used, followed by a neighbor-joining tree, to help visualize clustering of related genes and to identify orthologues and paralogues.

Alternatively, homologues, orthologues and paralogues may be identified by domain searches for a trehalose synthase domain, and for one of the phosphatase domains. The full-length protein sequence is then compared with SEQ ID NO:4, using bl2seq (Tatusova and Madden, 1999). Using this alignment, an orthologue or paralogue has at least 50% identities, preferably 55% identities, more preferably 60% identities. As non-limiting examples, AtTPS8 orthologues are present in *Oryza sativa* (Genpept accession numbers ABF94728, BAF06162 and BAF11342), *Brassica oleracea* (Genpept accession number ABD65165), *Medicago trunculata* (Genpept accession number ABE86430), *Cypripedium parviflorum* (Genpept accession number AAN86570) and *Ginlo biloba* (Genbank accession number AAX16015).

In one preferred embodiment, TPS is AtTPS8 (SEQ ID NO:4). In another preferred embodiment, TPS is AtTPS5 (SEQ ID NO: 1).

Preferably, the use is an inactivation of the TPS activity, and modulation is an increase in plant biomass and/or plant yield. Methods to inactivate the TPS activity are known to the person skilled in the art and include, but are not limited to, the knock out of the gene, the use of RNAi, gene silencing, knock out of the TPS promoter, inactivating mutations in the TPS promoter or in the coding region, or the synthesis by the plant of inactivating antibodies against TPS. Preferably, increase of plant biomass and/or plant yield is realized by increased root growth, increased stem thickness, increased leaf number and/or increased seed size. One preferred embodiment is the use of TPS to modulate plant growth, whereby modulation is obtained in absence of light. The term "yield," in general, means a measurable product of economic value, typically related to a specified crop, to an area, and to a period of time. Individual plant parts directly contribute to yield based on their number, size and/or weight, or the actual yield is the yield per acre for a crop and year, which is determined by dividing total production (includes both harvested and appraised production) by planted acres. The terms "increase," "improve" or "enhance" are interchangeable and shall mean in the sense of the application at least a 5%, 6%, 7%, 8%, 9% or 10%, preferably at least 15% or 20%, more preferably 25%, 30%, 35% or 40% more yield and/or growth in comparison to control plants as defined herein. Increased seed yield may manifest itself as one or more of the following: a) an increase in seed biomass (total seed weight), which may be on an individual seed basis and/or per plant and/or per hectare or acre; b) increased number of flowers per plant; c) increased number of (filled) seeds; d) increased seed filling rate (which is expressed as the ratio between the number of filled seeds divided by the total number of seeds); e) increased harvest index, which is expressed as a ratio of the yield of harvestable parts, such as seeds, divided by the total biomass; and f) increased thousand kernel weight (TKW), which is extrapolated from the number of filled seeds counted and their total weight. An increased TKW may result from an increased seed size and/or seed weight, and may also result from an increase in embryo and/or endosperm size.

Another aspect of the invention is the use of a plant class II TPS, as defined above, for the modulation of starch synthesis. Preferably, the use is the inactivation of TPS activity, and modulation is an increase in starch synthesis. Preferably, TPS is a class II TPS, according to the classification in *Arabidopsis thaliana*. A class II TPS comprises both a trehalose-6-phosphate synthase-like domain, as well as a trehalose-6-phosphate phosphatase-like domain (Leyman et al., 2001; Vogel et al., 2001). Even more preferably, TPS is selected from the group consisting of SEQ ID NOS:1-15 (TPS5-11, rice orthologue, poplar orthologue). In one preferred embodiment, TPS is AtTPS8 (SEQ ID NO:4). In another preferred embodiment, TPS is AtTPS5 (SEQ ID NO:1).

Still another aspect of the invention is a method for improving various yield-related traits in plants relative to control plants, comprising modulating expression and/or translation in a plant of a Class II TPS nucleic acid and/or a Class II TPS polypeptide, wherein modulated expression consists of a reduction or substantial elimination of expression and/or translation of an endogenous Class II TPS gene in a plant. As a non-limiting example, reduction or substantial elimination may be obtained by RNA-mediated silencing of gene expression, by co-expression, by the use of antisense class II TPS nucleic acid sequences or by the use of inverted repeats of class II TPS nucleic acids, preferably inverted repeats forming a hairpin structure.

Still another aspect of the invention is the method for the production of a transgenic plant having increased yield relative to control plants, which method comprises:
(i) introducing and expressing in a plant a genetic construct comprising one or more control sequences for reducing expression and/or translation in a plant of an endogenous Class II TPS gene; and
(ii) cultivating the plant, plant part or plant cell under conditions promoting plant growth and development.

"Control sequences," as used herein, are sequences that influence the expression and/or translation of the class II TPS gene, are known to the person skilled in the art, and include, but are not limited to, sequences causing co-expression, sequences encoding antisense RNA, and RNAi.

Still another aspect of the invention is a plant, obtainable according to the method of the invention, whereby the plant has reduced expression of an endogenous Class II TPS gene due introduction into a plant of a Class II TPS control nucleic acid sequence. "Reduced expression," as used herein, is an expression that is substantially decreased when the expression is compared with a non-transformed control plant, grown under the same conditions. Methods to measure expression are known to the person skilled in the art; a substantial reduction is a reduction with preferably 10%, more preferably 20%, even more preferably 30%.

BRIEF DESCRIPTION OF THE FIGURES

FIG. 1: Root length of AtTPS8 KO on MS medium, with and without sucrose, in light and in the dark. GT2, GT4 and GT6 are different KO lines of AtTPS8.

FIG. 2: Expression levels of AtCYCD3 and ApL3 in the AtTPS8 KO background.

FIG. 3: Phenotypic characterization of the adult AtTPS8 KO compared to WT plants.

DETAILED DESCRIPTION OF THE INVENTION

Examples

Materials and Methods to the Examples

Plant Material for AtTPS8

Figure 4:
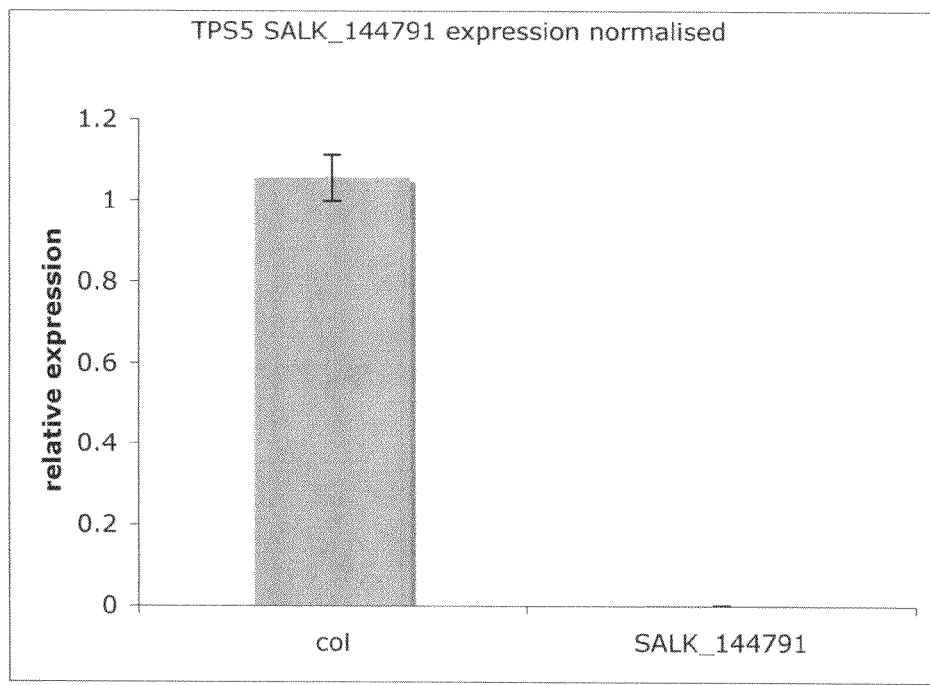
FIG. 4: SALK_144791 AtTPS5 expression data.

Wild-type *Arabidopsis* plants (Columbia) were transformed with silencing and over-expression constructs (see further). In addition, a Gene Trap line (GT13138, Landsberg erecta) was obtained through Martienssen's lab at Cold Spring Harbor Laboratory. To study the phenotype of these plants, homozygous lines were obtained. Seeds were surface sterilized and germinated in vertically oriented Petri dishes on 1× Murashige and Skoog medium (Duchefa) solidified with purified agar (Duchefa), with 1% sucrose or without sucrose (as indicated in the figures), in a daily cycle of 12 hours at 22° C. and 12 hours of darkness at 18° C. Ten days after germination, root length of plants was measured. Plants grown in dark conditions were kept in dark over the whole period of time.

Constructs

For the silencing of AtTPS8 (At1g70290) in *Arabidopsis*, the Gateway vectors, pDONR207 and pK7GWIWG2 (Karimi et al., 2002) were used. 149 bp of an AtTPS8-specific sequence was amplified with two primers containing the recombination sites AttB1 and AttB2. Forward primer, GGG-GACAAGTTTGTACAAAAAAGCAGGC-TCCGAAG-TAACTTCTACCTCC (SEQ ID NO: 18); Reverse primer, GGGGACCACTTTGTACAA-GAAAGCTGGGTCCCATCTCTAAGTTGTAACTG (SEQ ID NO:19). The construct was transformed in competent *Agrobacterium* cells (strain C58C1), and transformed in WT *Arabidopsis* plants using the flower dip method (Clough, 2005). T0 seeds were selected on kanamycin and transferred to soil to set seeds. These T1 seeds were again selected on kanamycin and screened for homozygous T2 lines.

The over-expression construct of AtTPS8 was made using a PCB302 plant vector. Full-length AtTPS8 was amplified from protoplast cDNA with the following primers: forward primer, CGGGATCCATGGTGTCAAGATCTTGTGCTAA (SEQ ID NO:20); reverse primer, AAGGCCTAACGAT-GCTTTCAAATGCAACTT (SEQ ID NO:21). The construct was transformed in *Agrobacterium* and plants as described above.

Gene Trap Line

The gene trap line (GT13138, Landsberg erecta) was obtained from Martienssen's lab at Cold Spring Harbor Laboratory. A pWS32 vector containing a Ds-transposable element with the β-glucuronidase (GUS) gene as a reporter and the Neomycin phosphotransferase (NPTII) gene as a selectable marker, was transformed in *Arabidopsis*, where it randomly inserted into the genome. Glucuronidase assays revealed insertions into exons of different genes. Insertion sites were then amplified by TAIL PCR (Liu et al., 1995) and sequenced. These sequences were validated and annotated according to the sequence of the *Arabidopsis* genome.

Plant Material for AtTPS5

SALK line "SALK_144791" (*Arabidopsis thaliana*, ecotype Colombia) was available from the Alonso/Crosby/Ecker *Agrobacterium* T-DNA transformed plant collection and was ordered at NASC/ABRC. The T-DNA flanking DNA sequence was recovered and sequenced by the Salk Institute Genomic Analysis Laboratory (SIGnAL), USA, and was predicted to be in the first exon of the AtTPS5 gene (At4 g17770). The ordered sequence-indexed lines were segregating T3 lines. With the NTPII marker (kanamycin resistance) and PCR, homozygous plants were selected, hereinafter referred to as "line 070(2)" (forward primer: 5'TCCTGCTTATATC-CCACCTGAGC3' (SEQ ID NO:22); and reverse primer: 5'GCGCCGCTTAAAGAAGGAGAA3' (SEQ ID NO:23)). Sequences were obtained with the left border T-DNA primer (Lba1: 5'TGGTTCACGTAGTGGGCCATCG3' (SEQ ID NO:24)), and the T-DNA was found at position 923 relative to the START codon in the cDNA of AtTPS5.

Genetrap line GT12622 (*Arabidopsis thaliana*, ecotype Landsberg erecta) was ordered from the collection of transposon insertion lines produced at the Martienssen lab of Cold Spring Harbor Laboratory, USA (Sundaresan et al., 1995; Martienssen, 1998). The line was generated using the Dissociation transposons (Ds) from maize, engineered to carry a uidA (β-glucuronidase (GUS)) reporter gene and an NPTII (neomycin phophotransferase) kanamycin resistance gene. Gene trap reporter genes have no promoter, so that GUS expression can occur only when the reporter inserts within a transcribed chromosomal gene, creating a transcriptional fusion. These elements simultaneously monitor gene expression and disrupt endogenous gene function. The gene trap construct has a multiple splice acceptor fused to the GUS gene. Based on the flanking sequences of the insertion site obtained by TAIL-PCR, line GT12622 was predicted by CSHL to carry a unique insertion of a genetrap-transposable DS element somewhere at the end of the first exon of the AtTPS5 gene (At4 g17770). The delivered sequence-indexed lines were F3 seeds. With the kanamycin marker and PCR, homozygous AtTPS5 knock-out lines (F5) were obtained, hereinafter referred to as "lines GT4.1 and GT6.2." Gene-specific primers (forward primer: 5'TTGGGCGCG-TAGCTTTATAC3' (SEQ ID NO:25) and reverse primer: 5'CAAGAAGATATGAAAACAGCCTCA3' (SEQ ID NO:26)) were designed, together with primers at the borders of the gene trap construct, to amplify specific flanking sequences of the insertion site. The accurate insertion place is at position 1930 (in the first exon) in the cDNA sequence of AtTPS5.

Example 1

TPS8 Knock-Out Lines Show Enhanced Growth Under Different Growth Conditions

In the yeast *Saccharomyces cerevisiae*, trehalose is synthesized in two reactions from UDP-glucose and glucose-6-phosphate by trehalose-6-phosphate synthase (encoded by TPS1) and trehalose-6-phosphate phosphatase (encoded by TPS2). In the *Arabidopsis thaliana* genome, 11 TPS-like genes have been detected. Those genes can be grouped in two subfamilies, displaying most similarity either to yeast TPS1 (encoding TPS in yeast; class I) or TPS2 (encoding TPP in yeast; class II) (Leyman et al., 2001). Almost nothing is known about the TPP-like class II genes in *Arabidopsis*. To study the effect of these genes, knock-out lines (KO), RNAi lines and over-expression lines were constructed and studied as described in materials and methods.

The lines were tested on 1× Murashige and Skoog medium (Duchefa) solidified with purified agar (Duchefa) (MS), with or without addition of sucrose. Representative knock-out lines were analyzed after ten days of germination. The results for the AtTPS8 KO are summarized in FIG. 1. Independent of the growth conditions, the KO line always showed a significant increase in root length, although the effect is slightly more pronounced when sucrose was present in the medium.

Example 2

TPS8 Inactivation Promotes CYCD3 and ApL3 Expression

To analyze the underlying mechanism of the increase in growth, the effect of the AtTPS8 KO on the expression of the cell cycle gene AtCYCD3 and on the starch biosynthesis gene ApL3 was studied by real time PCR. Compared to wild-type (wt), the expression of both ApL3 and AtCYCD3 was significantly higher. The results are shown in FIG. 2. The ApL3 result is especially unexpected, as Kolbe et al. (2005) have recently shown that T6P is inducing starch synthesis, whereas one would rather expect that the concentration of T6P is lower in the AtTPS8 KO.

Example 3

TPS8 Inactivation Results in Higher Biomass and Bigger Plants

Wild-type and AtTPS8 KO seedlings were put in soil, and were grown for 30 days, to compare the phenotypes of the adult plants. Adult AtTPS8 KO seedlings grow faster in soil, they have more but smaller rosette leaves and the inflorescence stem is twice as thick than the one in wild-type. The KO has approximately two times as much siliques as wt. The cauline leaves of the KO are much larger and look more like rosette leaves (FIG. 3). This leads to a higher seed yield and a higher overall biomass yield of the plant.

Example 4

TPS5 Inactivation Promotes Root Growth

Figure 5:
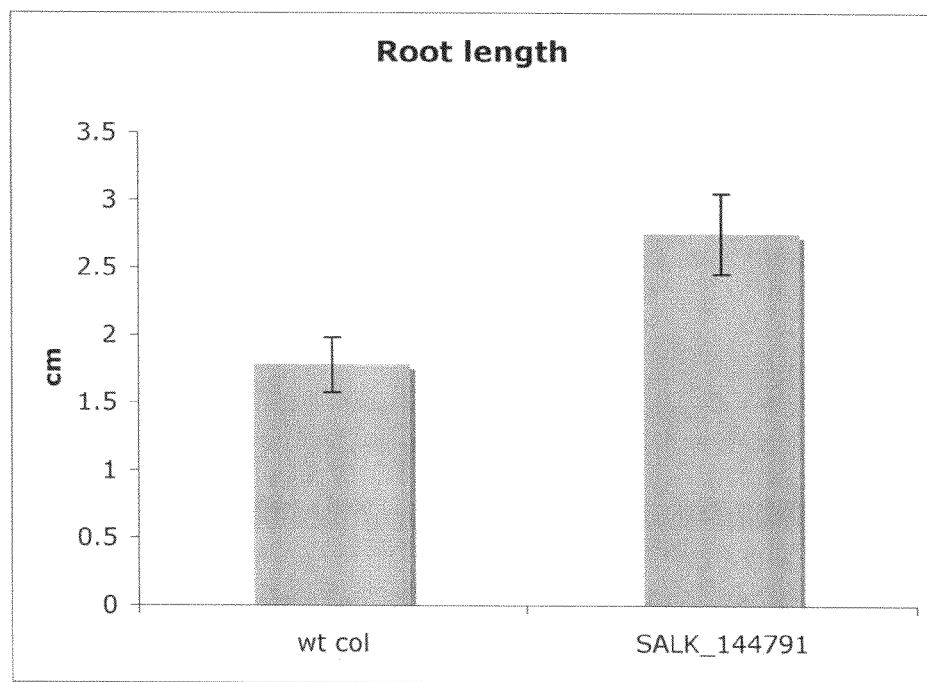
FIG. 5: root length measurements of SALK_144791 line.
Figure 6:
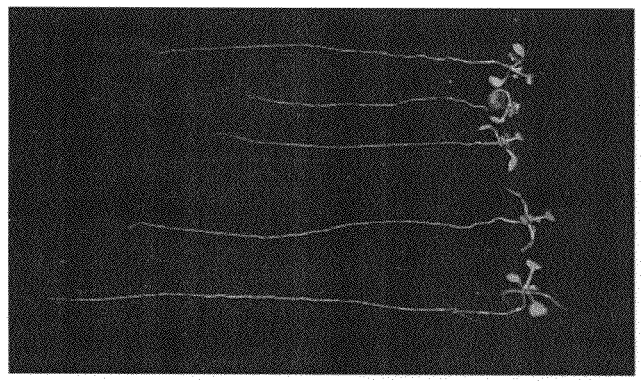
FIG. 6: Phenotype of the SALK_144791 AtTPS5 KO line, in comparison with WT (Columbia), on 1×MS, 1% sucrose medium.
Figure 7:
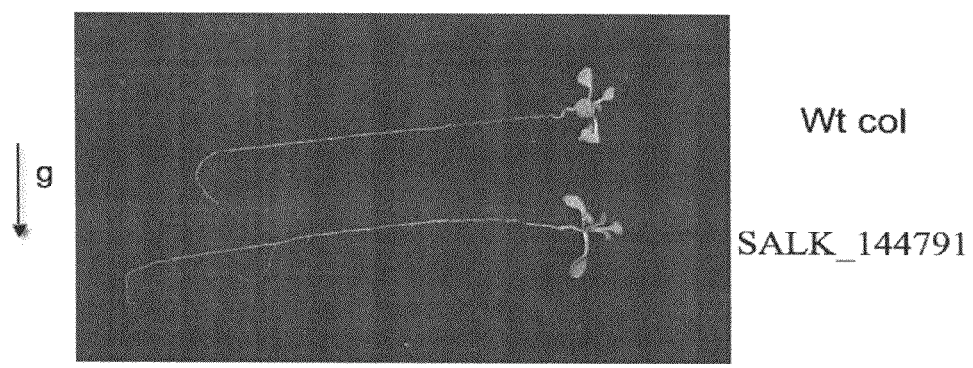
FIG. 7: Phenotype of the SALK_144791 AtTPS5 KO line, in comparison with WT (Columbia), on 1×MS, 1% sucrose medium: test on agravitrophic effect.

To test the expression of AtTPS5 in the homozygous SALK_144791 line, RNA was isolated from 50 seedlings of line 070(2). RT-PCR experiments (Forward primer: 5'GCACTCCTCAACGCTGATTT3' (SEQ ID NO:29) and Reverse primer: 5'AAGCCCTATGGTTCCACGTT3' (SEQ ID NO:30)) on cDNA demonstrated dramatic down-regulation of AtTPS5 expression (FIG. 4). For the phenotypic characterization, seeds of line 070(2) were damp-sterilized (100 ml bleach+3 ml HCL 37%) for four to six hours and imbibed/stratified for two days in constant light at 4° C. After two days, seeds were put on sterile plant medium plates (1×MS medium pH 5.7 (KOH), 1% sucrose) and incubated vertically in a growth chamber with 12 hours-12 hours light-dark cycle, 70 microE, 22° C. day, 18° C. night. After seven days of germination, root lengths of 18 seedlings were measured. The SALK lines showed a significant increase in root length (FIG. 5). This result was confirmed in a second experiment; pictures of the seedlings were taken after 13 days of germination (see FIG. 6). The seedlings appeared to have somewhat longer roots. However, this needs to be confirmed. Some plates were turned 90° C. to check possible gravitrophic effects. After four days, no agravitrophic effect was detected (FIG. 7).

Example 5

Genetrap TPS5 Inactivation Promotes Root and Hypocotyl Growth

Figure 8:
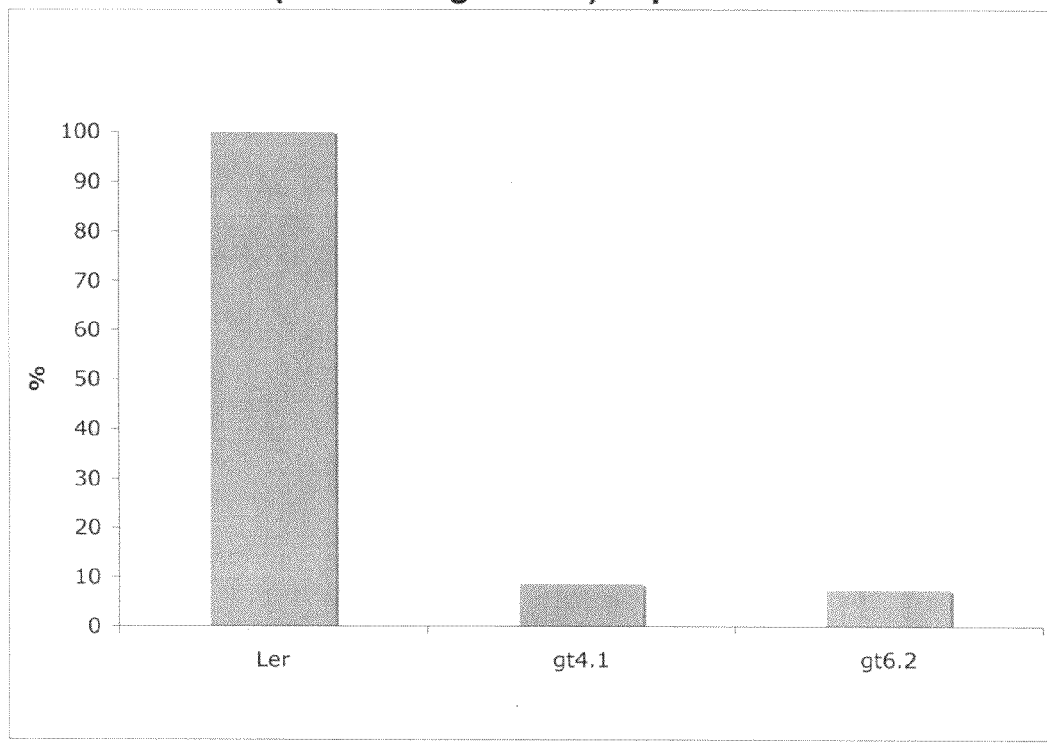
FIG. 8: GT12622 AtTPS5 expression data.
Figure 9:
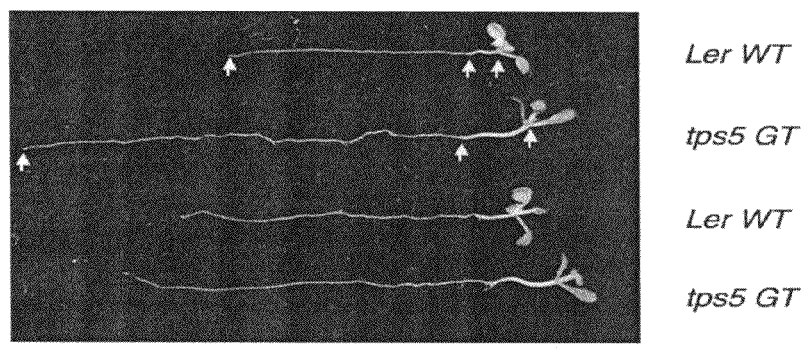
FIG. 9: Phenotype of Genetrap GT12622 AtTPS5 KO line, in comparison with WT (Landsberg erecta), on 1×MS, 1% sucrose medium.
Figure 10:
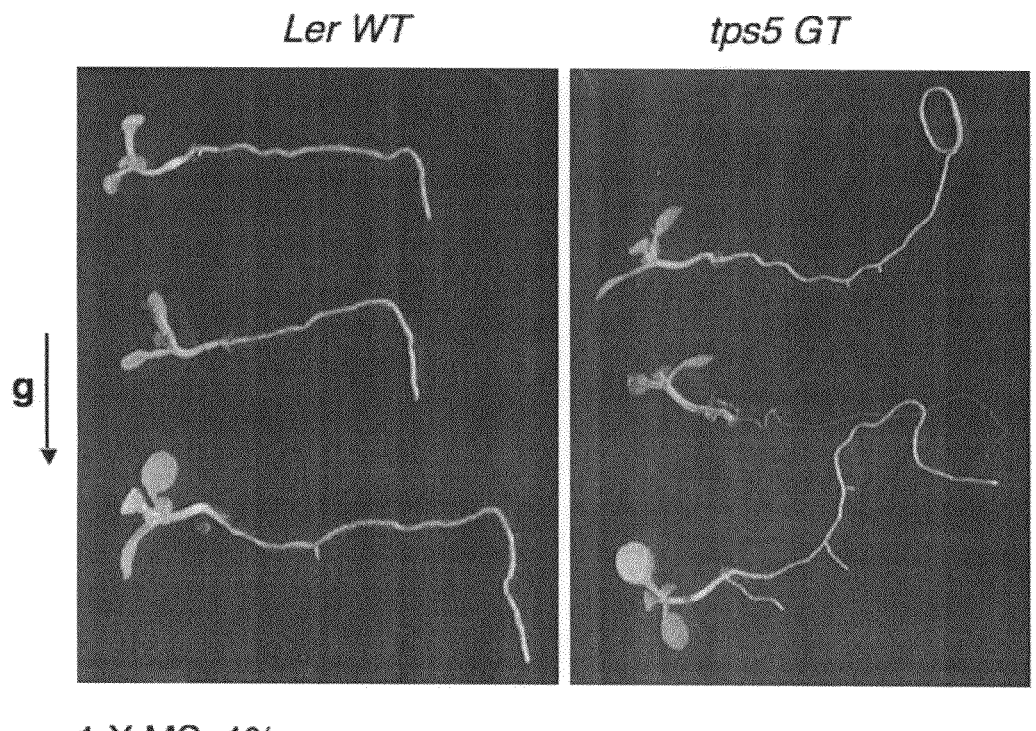
FIG. 10: Phenotype of Genetrap GT12622 AtTPS5 KO line, in comparison with WT (Landsberg erecta), on 1×MS, 1% sucrose medium: test on agravitrophic effect.

To test the expression of AtTPS5 in the homozygous TPS5 Genetrap lines, RNA was isolated from 50 seedlings of two GT knock-out lines. RT-PCR (Forward primer: 5'GCACTC-CTCAACGCTGATTT3' (SEQ ID NO:29) and Reverse primer: 5'AAGCCCTATGGTTCCACGTT3' (SEQ ID NO:30)) demonstrated dramatic down-regulation of AtTPS5 expression (FIG. 8). Seeds were damp-sterilized (100 ml bleach+3 ml HCL 37%) for four to six hours and imbibed/stratified for two days in constant light at 4° C. After two days, seeds were put on sterile plant medium plates (1×MS medium pH 5.7 (KOH), 1% sucrose) and incubated vertically in a growth chamber with 12 hours-12 hours light-dark cycle, 70 microE, 22° C. day, 18° C. night. Ten days after germination, pictures were taken of seedlings (FIG. 9). The seedlings appeared to have significantly longer roots and longer hypocotyls. Several days after turning the plates 90° C., and contrary to what was seen in Columbia, seedlings showed agravitrophic effects (FIG. 10).

References

Avonce N., D. Leyman, J. O. Mascorro-Gallardo, P. Van Dijck, J. M. Thevelein, and G. Iturriaga (2004). The *Arabidopsis* trehalose-6-P synthase AtTPS1 gene is a regulator of glucose, abscisic acid and stress signaling. *Plant Physiol.* 136:3649-3659.

Eastmond P. J., Y. Li, and I. A. Graham (2003). Is trehalose-6-phosphate a regulator of sugar metabolism in plants? *J. Exp. Bot.* 54:533-537.

Garg A. K., J. K. Kim, T. G. Owens, A. P. Ranwala, Y. D. Choi, L. V. Kochian, and R. J. Wu (2002). Trehalose accumulation in rice plants confers high tolerance levels to different abiotic stresses.

Jang I. C., S. J. Oh, J. S. Seo, W. B. Choi, S. I. Song, C. H. Kim, Y. S. Kim, H. S. Seo, Y. D. Choi, B. H. Nahm, and J. K. Kim (2003). Expression of bifunctional fusion of the *Escherichia coli* genes for trehalose-6-phosphate synthase and trehalose-6-phosphate phosphatase in transgenic rice plants increase trehalose accumulation and abiotic stress tolerance without stunting growth. *Plant Physiol.* 131:516-524.

Kolbe L., A. Tiessen, H. Schluepmann, M. Paul, S. Ulrich, and P. Giegenberger (2005). Trehalose-6-phosphate regulates starch synthesis via post-translational redox activation of ADP-glucose pyrophosphorylase. *Proc. Nat. Acad. Sci. USA* 102:11118-11123.

Leyman B., P. Van Dijck, and J. M. Thevelein (2001). An unexpected plethora of trehalose biosynthesis genes in *Arabidopsis thaliana*. *Trends Plant Sci.* 6:510-513.

Schluepmann H., T. Pellny, A. van Dijken, S. Smeekens, and M. Paul (2003). Trehalose-6-phosphate is indispensable for carbohydrate utilization and growth in *Arabidopsis thaliana*. *Proc. Natl. Acad. Sci. USA* 100:6849-6854.

Schluepmann H., A. van Dijken, M. Aghdasi, B. Wobbes, M. Paul and S. Smeekens (2004). Trehalose-mediated growth inhibition of *Arabidopsis* seedlings is due to trehalose-6-phosphate accumulation. *Plant Physiol.* 135:879-890.

Tatusova T. A. and T. L. Madden (1999). "BLAST 2 sequences—a new tool for comparing protein and nucleotide sequences." *FEMS Microbiol. Lett.* 174:247-250.

Vogel G., O. Fiehn, L. Jean-Richard-dit-Bressel, T. Boller, A. Wiemken, R. A. Aeschbacher, and A. Wingler (2001). Trehalose metabolism in *Arabidopsis*: occurrence of trehalose and molecular cloning and characterization of trehalose-6-phospate synthase homologues. *J. Experim. Botany* 52:1817-1826.

The invention claimed is:

1. A method of increasing a plant's growth, the method comprising:
inactivating a class II trehalose-6-phosphate synthase to increase the plant's growth as compared with a control plant grown under the same conditions, wherein said trehalose-6-phosphate synthase comprises SEQ ID NO:4.

2. The method according to claim 1, wherein said increase is increased root growth, increased stem thickness, increased leaf number and/or increased seed size in the plant.

3. A method of modulating a plant's growth so as to increase plant biomass or plant yield, the method comprising:
inactivating plant class II trehalose-6-phosphate synthase in the plant, wherein the trehalose-6-phosphate synthase comprises SEQ ID NO: 4, so as to increase the plant biomass or plant yield.

4. The method according to claim 3, wherein inactivation of the plant class II trehalose-6-phosphate synthase in the plant is selected from the group consisting of (a) knock out of the plant class II trehalose-6-phosphate synthase gene, (b) utilizing RNAi with respect to the plant class II trehalose-6-phosphate synthase gene, (c) gene silencing of the plant class II trehalose-6-phosphate synthase gene, (d) knock out of the plant class II trehalose-6-phosphate synthase gene promoter, (e) inactivating mutations in the plant class II trehalose-6-phosphate synthase gene promoter, (f) inactivating mutations in the coding region of the plant class II trehalose-6-phosphate synthase gene, (g) inducing synthesis by the plant of inactivating antibodies against the plant class II trehalose-6-phosphate synthase, and (h) combinations of any thereof.

5. A method of modulating a plant's growth so as to increase plant biomass or plant yield, the method comprising:
inactivating a plant class II trehalose-6-phosphate synthase in the plant, wherein the plant class II trehalose-6-phosphate synthase comprises any one of SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 15,
so as to increase the plant biomass or plant yield.

6. The method according to claim 5, wherein said increase is obtained in absence of light.

* * * * *